(12) United States Patent
Rundell et al.

(10) Patent No.: US 8,326,887 B2
(45) Date of Patent: *Dec. 4, 2012

(54) REPORT GENERATION WITH INTEGRATED QUALITY MANAGEMENT

(75) Inventors: Marion Rundell, Seabrook, TX (US); John Orsburn, Spring, TX (US)

(73) Assignee: PP Associates, LP, Seabrook, TX (US)

( * ) Notice: Subject to any disclaimer, the term of this patent is extended or adjusted under 35 U.S.C. 154(b) by 1 day.

This patent is subject to a terminal disclaimer.

(21) Appl. No.: 12/977,518

(22) Filed: Dec. 23, 2010

(65) Prior Publication Data

US 2011/0093445 A1   Apr. 21, 2011

Related U.S. Application Data

(63) Continuation of application No. 11/279,005, filed on Apr. 7, 2006, now Pat. No. 7,861,159.

(51) Int. Cl.
*G06F 17/30* (2006.01)

(52) U.S. Cl. ........ 707/802; 707/803; 707/804; 724/246; 724/247

(58) Field of Classification Search .......... 707/802–804; 704/246

See application file for complete search history.

(56) References Cited

U.S. PATENT DOCUMENTS

| | | |
|---|---|---|
| 6,304,848 B1 | 10/2001 | Singer |
| 6,726,620 B2 | 4/2004 | Shibata et al. |
| 6,813,603 B1 * | 11/2004 | Groner et al. ................. 704/235 |
| 6,834,264 B2 | 12/2004 | Lucas et al. |
| 6,973,477 B1 * | 12/2005 | Martino ........................ 709/203 |
| 6,980,871 B1 | 12/2005 | Sweat |
| 7,028,265 B2 | 4/2006 | Kuromusha et al. |
| 7,188,072 B2 | 3/2007 | Eichstaedt et al. |
| 7,254,581 B2 | 8/2007 | Johnson et al. |
| 7,379,946 B2 | 5/2008 | Carus et al. |
| 7,395,214 B2 | 7/2008 | Shillingburg |
| 7,436,311 B2 | 10/2008 | Rapaport et al. |
| 7,447,632 B2 | 11/2008 | Itou |
| 7,484,661 B2 | 2/2009 | Shinkai |
| 7,996,759 B2 * | 8/2011 | Elkady ........................ 715/225 |
| 2002/0029155 A1 * | 3/2002 | Hetzel et al. ................... 705/2 |
| 2002/0133488 A1 * | 9/2002 | Bellis et al. ................... 707/6 |
| 2003/0130872 A1 | 7/2003 | Dvorak |
| 2003/0144885 A1 | 7/2003 | Sachdev |
| 2004/0052342 A1 * | 3/2004 | Jugovec et al. ............ 379/88.22 |
| 2004/0193049 A1 | 9/2004 | Greenberg |
| 2004/0254791 A1 * | 12/2004 | Coifman et al. .............. 704/246 |
| 2005/0075544 A1 | 4/2005 | Shapiro et al. |
| 2005/0102146 A1 * | 5/2005 | Lucas et al. .................. 704/270 |
| 2005/0177403 A1 | 8/2005 | Johnson |
| 2006/0161460 A1 | 7/2006 | Smitherman et al. |
| 2006/0259392 A1 | 11/2006 | Rabenold et al. |
| 2006/0265221 A1 | 11/2006 | Howes |
| 2007/0011608 A1 | 1/2007 | Titemore et al. |
| 2007/0232868 A1 | 10/2007 | Reiner |

FOREIGN PATENT DOCUMENTS

| | | |
|---|---|---|
| EP | 1372102 | 12/2003 |
| WO | 0201778 | 1/2002 |
| WO | 03086304 | 10/2003 |
| WO | 2004104742 | 12/2004 |

OTHER PUBLICATIONS

Larry V. Allen, "Scripting for Dragon NaturallySpeaking 8, a Guide to Advanced Scripting for Dragon NaturallySpeaking 8.x", Softnet Systems, Inc. (USA) (Dec. 2004) (pp. i-viii, 1-157).

Raouf E. Nakhleh, M.D. (Editors), "Quality Management in Anatomic Pathology, Promoting Patient Safety Through Systems Improvement Error Reduction", College of American Pathologists (USA) (2005) (Glossary Not Included) (pp. i-xi, 1-182).

Rachna S. Desai, PCT/ISA/210, International Search Report for International App. No. PCT/US07/66100, Oct. 9, 2008, 4 pages.

Rachna S. Desai, PCT/ISA/237, Written Opinion of the International Searching Authority for International App. No. PCT/US07/66100, Oct. 9, 2008, 3 pages.

Supplemental European Search Report and Search Opinion for EP Application No. 07760219, Jan. 4, 2010, 11 pages.

* cited by examiner

*Primary Examiner* — Hanh Thai

(74) *Attorney, Agent, or Firm* — Wong, Cabello, Lutsch, Rutherford & Brucculeri, LLP

(57) ABSTRACT

Reports are generated by a computing engine using user inputs to a template and automatically added quality management values. Quality management reports can be automatically generated at selected intervals, such as daily, monthly, and yearly. Users are thus able to meet required quality assurance standards.

31 Claims, 14 Drawing Sheets

REPORT GENERATION WITH INTEGRATED QUALITY MANAGEMENT

CROSS-REFERENCE TO RELATED APPLICATIONS

The present application is a continuation of U.S. patent application Ser. No. 11/279,005, filed Apr. 7, 2006, issued as U.S. Pat. No. 7,861,159 on Dec. 28, 2010, which is incorporated by reference in its entirety for all purposes.

BACKGROUND OF THE INVENTION

1. Field of the Invention

The present invention relates to methods and systems for generating reports that integrate values from databases and include quality management information, and more particularly to systems and methods for generating pathology reports with sufficient quality management to meet required standards.

2. Description of the Related Art

Producing reports by longhand can be a tedious, time-consuming production. Inventions such as shorthand and dictation with transcription shortened the amount of time required to generate reports.

Dictation software such as Dragon's Naturally Speaking and IBM's Via Voice have evolved to include advanced versions that allow for limited command control functionality such as Via Voice's macro commands and voice commands. Not only is the data from the report transcribed by the software, but also the software has a limited ability to allow the user to dictate commands to the software so the software can provide formatting or move around within the text without any intervention by the user.

In the modern world standards, regulations, and often statutes require certain amounts of quality assurance or quality control of various reports that affect people's lives. Typical quality assurance requirements sampling five or ten percent of the total number of reports that are generated to determine if the reports are being properly generated. Any sampling scheme requires that the sample be chosen carefully so that it is representative of the original population, here the total number of reports generated.

Starting about 1990, pathologists started using computer dictation software to generate reports. The general problem with using dictation software, or the dictation in general that the software replaced, was that useful quality assurance reports were difficult and time consuming to generate.

It would be advantageous to have a system and method of generating reports that provided better quality management than those currently available.

BRIEF SUMMARY OF THE INVENTION

According to one aspect of the present invention, a system is provided that includes a configurable data retrieval device and an input device configured to receive data and one or more commands. The system also includes a computing engine coupled to the input device for at least a period of time. The computing engine receives data in one or more commands from the input device, and the computing engine is configured to access the configurable data retrieval device. The computing engine is further configured to generate a report, where the report includes data, values retrieved from the configurable data retrieval device in response to at least one of the one or more commands, and quality management values determined by the computing engine. The computing engine is further configured to store the data in one or more selected locations in the configurable data retrieval device in response to selected ones of the one or more commands.

According to another aspect of the present invention, a method of creating a report is provided. The method includes using an input device to enter notes about one or more observations. The notes include one or more commands on how to present the one or more observations in the report. The method also includes a device receiving the notes from the input device, and the device extracting the one or more commands from the notes and arranging the one or more observations in the report based on the one or more commands. The method further includes the device adding one or more quality management values to the report and generating the report.

In still another aspect of the present invention, a database system is provided that includes a first set of records, where each entry of the first set of records corresponds to a data entry of a category in the first set. The database system also includes a second set of records, where each entry of the second set of records corresponds to a command of a category in the second set. Each command of the category in the second set includes a corresponding code. The database system also includes a database engine configured to retrieve a string of values, where each of the string of values corresponds to either an entry in the first set or a code in the second set. The database engine is further configured to respond to the code with a corresponding command from the second set of records. The database engine is further configured to respond to select data entries with one or more quality management values in addition to one or more records in the first set of records and the second set of records.

In yet another aspect of the present invention, another method of generating reports is provided. The method includes providing a plurality of data fields editable by a user inputting notes with a data input device and providing navigation by the user with the data input device direct to any of the plurality of data fields. The method also includes capturing the notes from the input device in a database format and providing automatic reporting by electronic transmission.

BRIEF DESCRIPTION OF THE SEVERAL VIEWS OF THE DRAWINGS

Various aspects of the present invention will become apparent and more readily appreciated from the following description of the presently preferred exemplary embodiments, taken in conjunction with the accompanying drawings, of which.

DETAILED DESCRIPTION OF THE INVENTION

As used herein, the following terms are to be given the following definitions when interpreting the specification and drawings. A user includes a person or machine that provides input through the input device. An observation includes what the user saw, determined, or calculated, using any available natural, augmented, or artificial sense. Notes include observations, commands, and/or indications of observations and/or commands. A computing engine includes a device, computer, or network-attached device or computer that provides computing power to manipulate the input from the input device, retrieve entries from a database, storage, or over a network, and/or compare, compute, or calculate values based in any way on the input or stored values, such as quality management metrics. Data include any one or more datum, so "data" is a general term referring to any one or more values, observations, or notes. A command includes data used by a computing engine to indicate a location in storage, a decision parameter, and/or an indication of steps of or a complete process to be performed. An auto-update mechanism includes a way of updating more than one local and/or remote records without user intervention. When any one linked record is changed, all linked versions of that record are changed by the auto-update mechanism. The auto-update mechanism updates in only in one direction, from a changeable entry to linked entries. Databases may include flat file databases or may include multiple layer databases or relational databases. An entry in a database may be a pointer to another database, a data entry, or a command code that indicates to a database engine that a command needs to be performed as opposed to data being entered into the report or template.

Figure 1A:
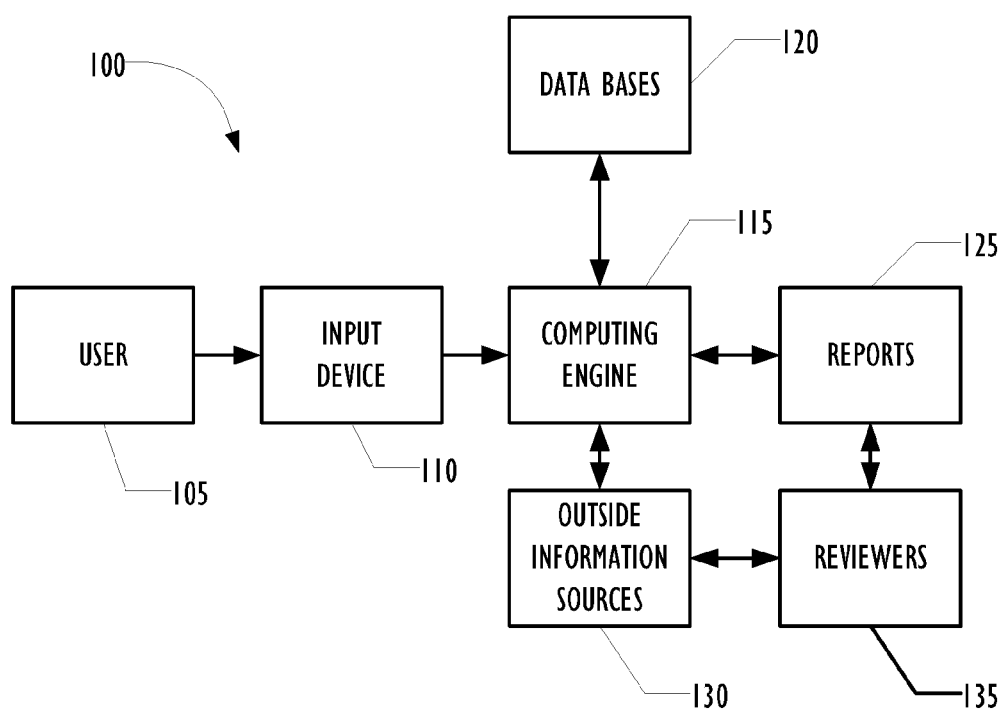
FIG. 1A is a general data flow diagram for report generation, according to one embodiment of the present invention.

As shown in FIG. 1A, the general flow diagram 100 of one embodiment of the present invention shows a user 105 providing data, observations, notes, commands, and/or other values to or through an input device 110. The input device 110 provides the user's data, observations, commands, and/or values to a computing engine 115. In addition, the computing engine 115 may read values from one or more databases 120 and/or outside information stores 130. The computing engine 115 may also store the user's data, observations, commands, and/or values in one or more databases 120 or an information store of the outside information stores 130. The computing engine 115 combines the input from the user(s), provided through the input device 110, with entries in the databases 120 and/or entries in the outside information stores 130 into one or more reports 125. One or more reviewers 135, who may or may not have access to the outside information stores 130, may review the reports 125. A reviewer of the reviewers 135 may become a user 105 in generating a report of the reports 125. Note that databases 120 and/or the remote information stores 130 may be local to the user or remotely accessed through a network of some kind.

The input device 110 may differ in different embodiments of the present invention. In one embodiment, the input device 110 is a voice dictation and transcription device or system. For some uses, silence may be more important than being hands-free. In another embodiment, the input device 110 is a real or virtual touch screen or touch pad, including one projected into space or onto a surface. In some instances, the hands will provide more useful input than the voice. In still another embodiment, the input device 110 is a stylus on a screen or surface, or other handwriting recognition system. Other input devices 110 are also contemplated, as would be apparent to those of skill in the art having the benefit of this disclosure.

According to various embodiments of the present invention, the input device 105 is a microphone, which feeds into a computing engine 115 for handling voice recognition and for handling database calculations. The microphone needs to be usable for speech recognition. In one embodiment, a boom microphone may be used. In another embodiment, a headset microphone may be used. Other microphone types may be used as desirable.

Figure 1B:
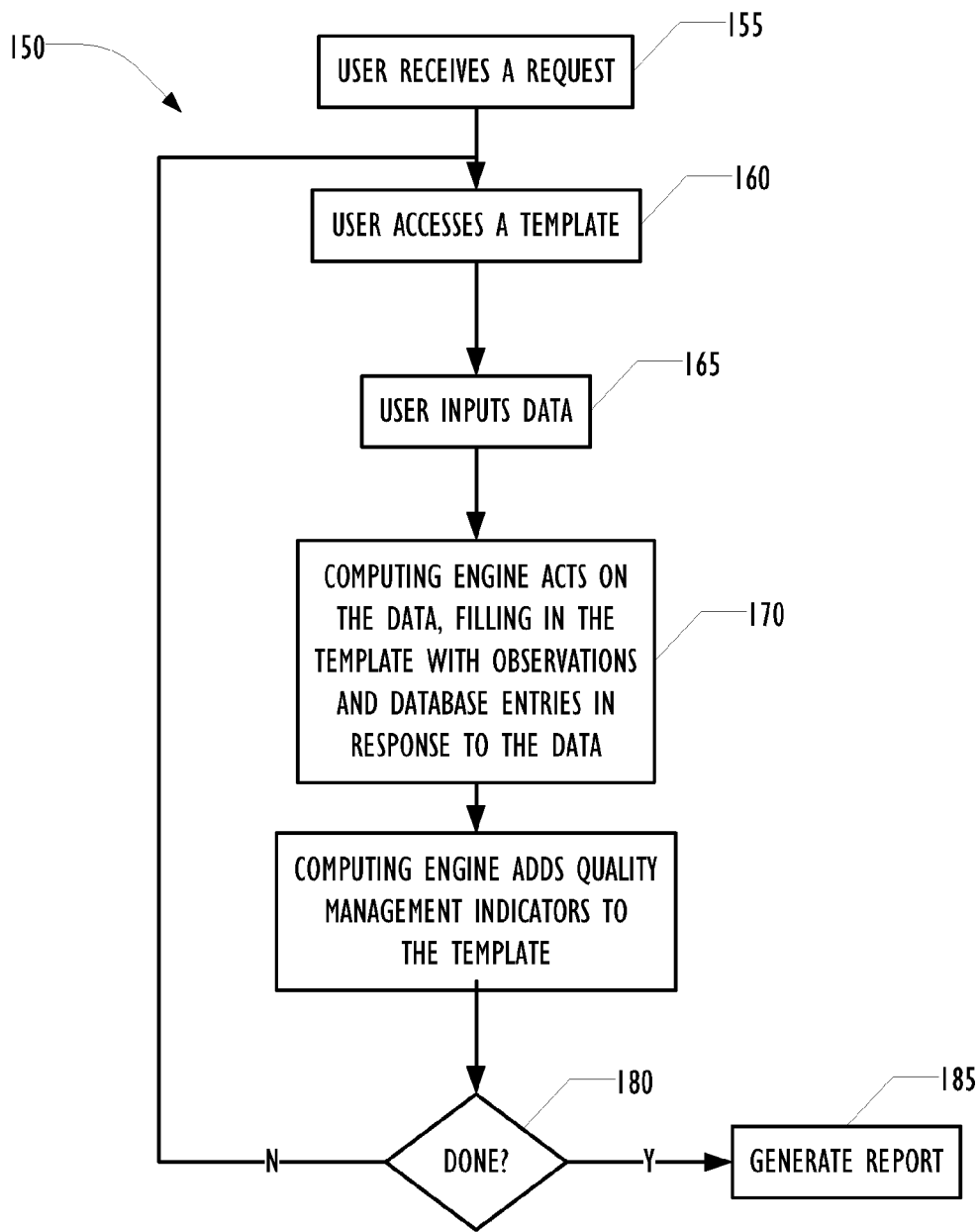
FIG. 1B is a flowchart of a general method of report generation, according to one embodiment of the present invention.

Turning now to FIG. 1B, a general method 150 of generating reports with integrated quality management indicators is shown. The method 150 starts with a user, such as the user 105 in FIG. 1A, receiving a request to generate a report of some type, block 155. In various exemplary and illustrative embodiments of the present invention, the report may be a pathologist's report on a slide specimen or a police officer's traffic incident report. The user 105 next accesses a template, block 160. In various embodiments of the present invention, a computing engine, such as the computing engine in FIG. 1A, may have access to any number of stored templates corresponding to any number of reports to be generated. The user 105 may have access only to the user's own templates, or the user 105 may have access to general global templates, or even to the templates available to all users of a given system. In one embodiment, the user 105 provides an indication of the desired template to the computing engine 115 using the input device 110, shown in FIG. 1A. The user 105 inputs data, block 165. In a preferred embodiment, the user inputs data using the input device 110. In other embodiments, the user may input the data using any data entry technique or apparatus.

According to the method 150, the computing engine 115 acts on the data, filling in the template with observations and database entries in response to the data, block 170. The data input by the user 105 may include any one or more of values, observations, commands, or notes, either known or provided by the user 105. The observations of the user 105 may be put in fields in the template by the computing engine 115. Other fields in the template may be filled by the computing engine 115 with database entries. The choice of databases 120 to be accessed or entries in a given database to be added to the template may be chosen based in response to the data provided by the user. The computing engine also adds quality management indicators to the template, block 175.

The quality management indicators added to the template, either permanently or temporarily, are added based on the template and/or the fields filled within the template. Examples of quality management indicators include mandatory error checking fields that are necessary for results to be saved and/or transferred, restricted entry fields that only accept a respective set of possible entries, and/or descriptive or quantitative fields. Example types of quality management indicator fields include status fields, prediction fields, source fields, comparison fields, correlation fields, referral fields, quantitative marker fields, recommended action fields, suitability fields, sample suitability fields, timing fields, reasons for delay fields, identification fields, location indicator fields, notification fields, adequacy fields, and timing fields.

Examples of actual pathology quality management indicators include: tissue status, slide code, slide acceptability, pre-match, tissue source, initial assessment, initial suspicion, impression of correlation, committee referral, cytomatch—comparison of cytology slide with tissue slide, recommended action based on cytomatch, suitability of sample for diagnosis, outside consult agreement, action based on outside consult, results, frozen specimen evaluation, action based on correlation of frozen specimen with diagnosis, number of frozen specimens, time to evaluation frozen specimen, delay in evaluation of frozen specimen, action based on delay, degree of difference in frozen specimen and final diagnosis, pathologist's identification, exam typist, final page of exam report indicator, notification to pathologist of possible difference from clinical indication, indication of lack of adequacy of specimen.

According to the method 150, the user 105 may be finished providing input, and a decision is made (at decision block 180) as to whether to continue to add more input (by returning to block 165) or to generate the report, block 185, such as one of the reports 125 of FIG. 1A. In some embodiments, for some paths through blocks 165-180, when the user 105 provides input in block 165, the computing engine does not have to add anything to the template in blocks 170 or 175. In some implementations of blocks 165-180, the user may provide data in 165 while the computing engine acts on the data in block 170 without adding quality management indicators in block 175, or the computing engine may act on the data in 170 but not add anything to the template in 170 and add quality management indicators to the template in block 175. The reports generated in block 185 may be any type of report. The report may be filed in a database 120, shown in FIG. 1A or an outside information store shown at 130 in FIG. 1A. In some embodiments, a report generated in block 185 will be transmitted electronically to a reviewer, such as one of the reviewers 135 shown in FIG. 1A.

Figure 2:
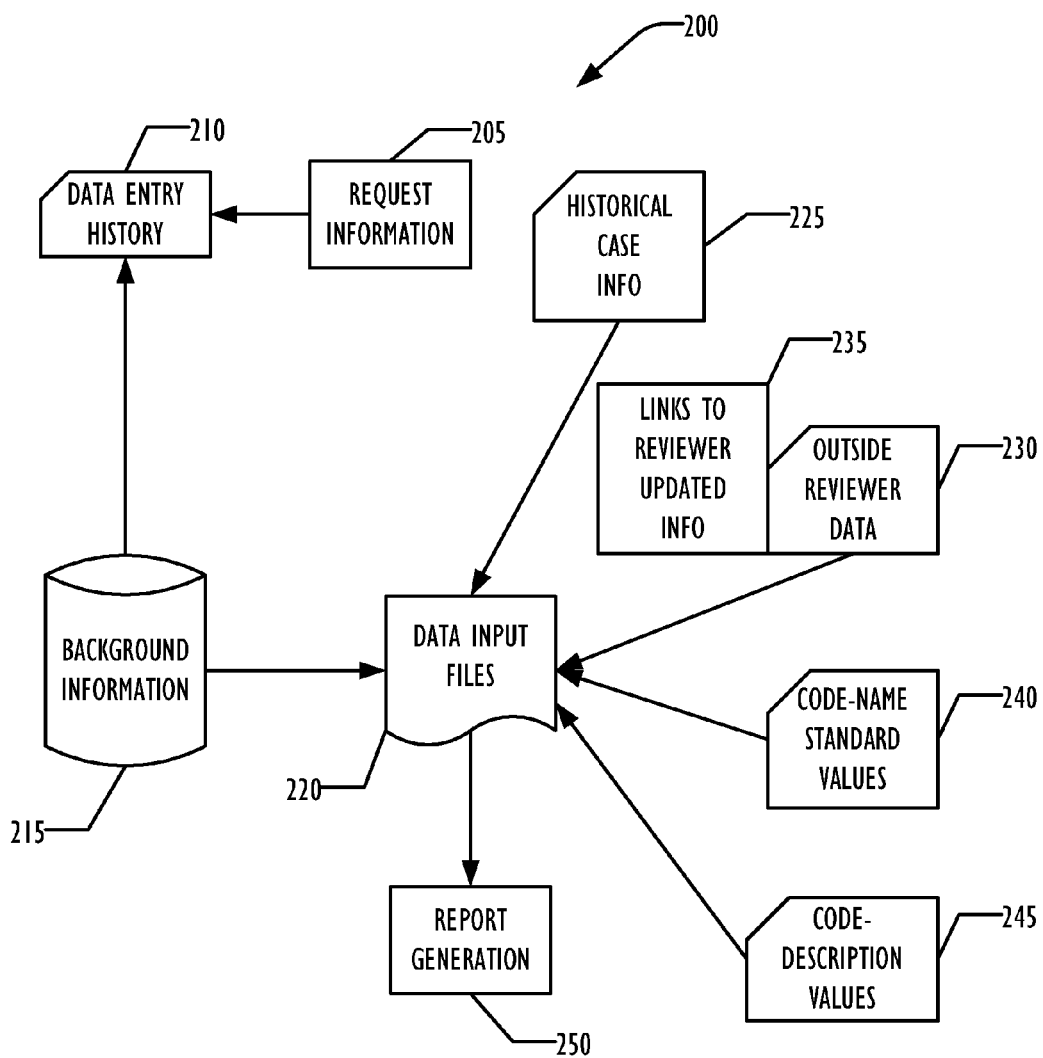
FIG. 2 is a data flow diagram of initial data collection in generating a report, according to one embodiment of the present invention.

Turning now to FIG. 2, an initial data collection flow diagram 200, according to one embodiment of the present invention, starts with a request for information 205. The request for information 205 may include information for which the user 105 will provide a response or observations. The request for information 205 may also include a description of people, places, or things to be observed, including times for the observations. The request for information 205 is provided to data entry history 210, where the user 105 is able to evaluate previous observations and entries made in the past. The data entry history 210 may be updated by a database of background information 215. The data entry history 210 and background information 215 are available to data input files 220 for integration. The data input files 220 may include data files from any number of sources related to the observations that are made by the user 105. The data input files 220 may also be updated by historical case information 225. The historical case information 225 may include historical data related to the request for information 205. The data input files 220 are linked so that updated data can be provided by outside reviewer's data 230. The data input files 220 are also able to receive entries from code-names standard values entries 240 and code-description values 245. The data input files 220 using the values available from the data entry history 210, the background information 215, the historical case information 225, the outside reviewer data 230, code-name standard values 240, and/or code-description values 245 work to generate reports 250. Outside reviewers' data 230, as well as possibly other values, is preferably updated with an auto-update mechanism 235.

Figure 3:
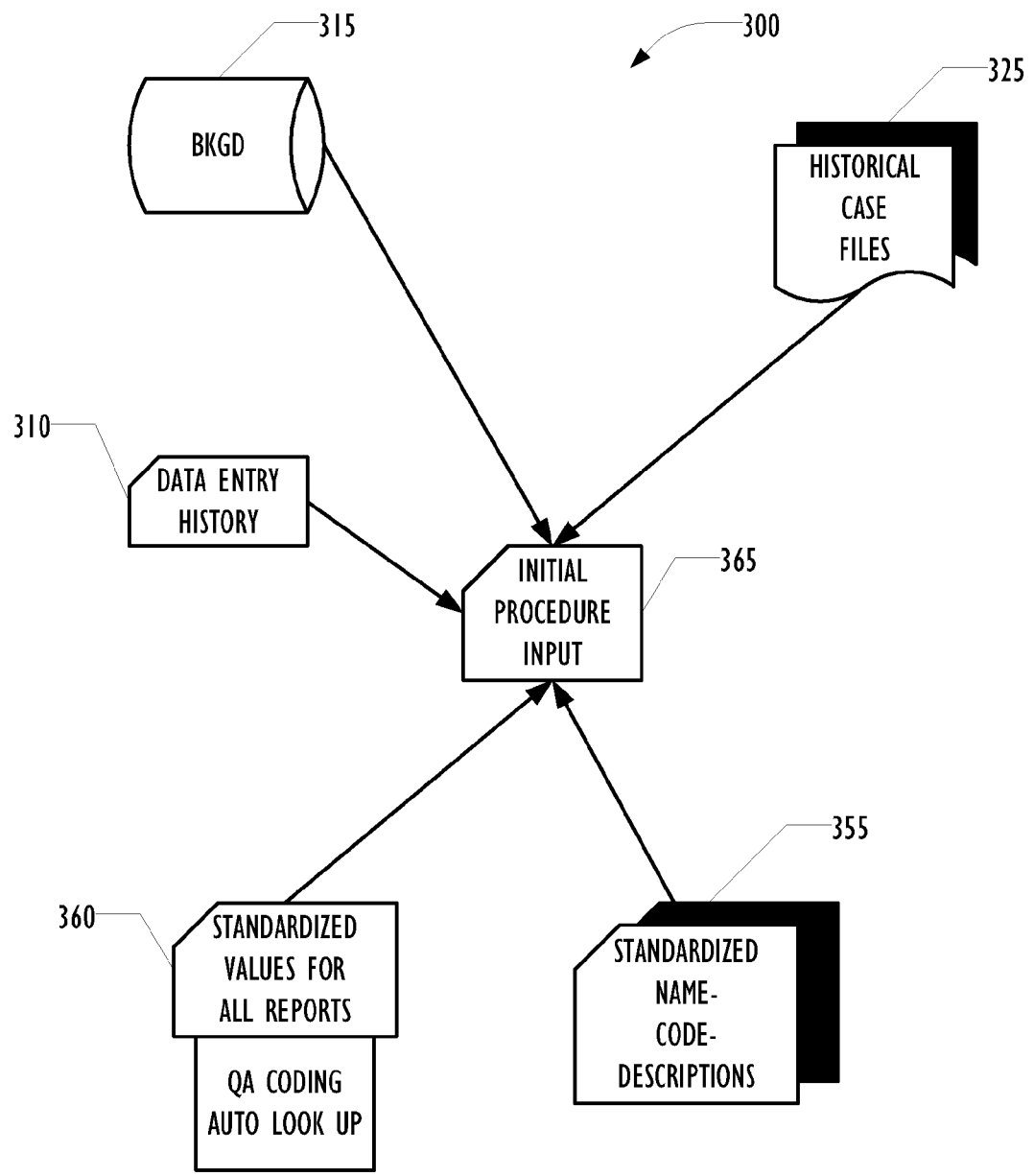
FIG. 3 is a data flow diagram of the initial procedure and input, according to one embodiment of the present invention.

Turning now to FIG. 3, general flow diagram 300 shows the initial procedure and input 365 receiving various values from various sources. These sources include background information 315, and the data entry history values 310. Values may also be received from the historical case files 325. Inputs may be received from standard values for all reports including quality assurance coding and automatic lookup values from entries 360. Values may also be received from the standardized name-code-description values 355. Integration of values into the initial procedure and input 365 preferably occurs by user input codes.

In one embodiment, the operations of FIG. 2 and FIG. 3 are performed separately. In this embodiment, the operations of FIG. 2 are followed by the operations of FIG. 3 and then the operations of FIG. 4 or FIG. 5. In this embodiment, separate log files may be created during or after the operations of FIG. 2 and the operations of FIG. 3.

In another embodiment, the operations of FIG. 2 and FIG. 3 are performed concurrently. In the concurrent embodiment, the method moves from the concurrent operations of FIG. 2 and FIG. 3 directly to the operation of FIG. 4 or FIG. 5. In this concurrent embodiment, unified log files may be created during or after the concurrent operations of FIG. 2 and FIG. 3.

Figure 4:
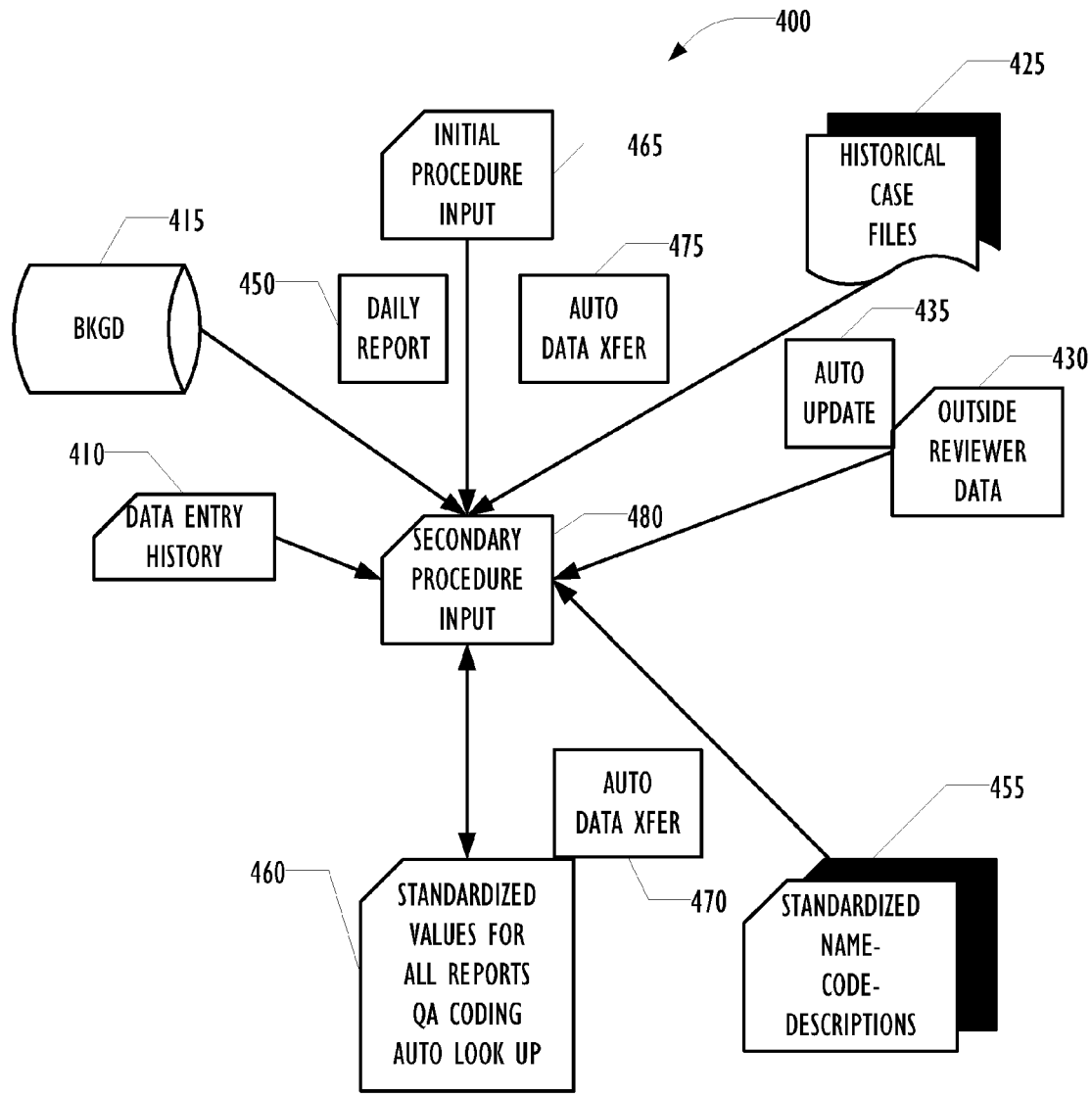
FIG. 4 is a data flow diagram of an optional secondary procedure and input values, according to one embodiment of the present invention.

FIG. 4 shows flow diagram 400, showing the inputs for the optional secondary procedures 480. Generally, values from the initial procedure 465 are provided in initializing the secondary procedure 480. Note that the initial procedures are generally provided by auto-update mechanism 475 into the secondary procedure values 480. As with the initial procedure 365 shown in FIG. 3, the secondary procedure 480 shown in FIG. 4, may receive input from the data entry history 410 and the background 415. Entries may also be received from the historical case files 425 and/or the outside reviewer data 430. The outside reviewer data 430 is typically provided using an auto-update 435 mechanism to provide new or updated values to the secondary procedure 480 from a storage device, such as one of the outside information stores 130, shown in FIG. 1A. Standard name-code-description values 455 are also provided at the secondary procedure 480, usually based on indications provided by the user 105 as data, such as in block 170, shown in FIG. 1B. Standardized values for all reports and quality assurance coding and auto-lookup 460 are provided on an auto-update basis 470 to the secondary procedure 480. Values from the secondary procedure 480 may also be stored as standardized values 460. The initial procedure 465 and secondary procedure 480 may be used to generate one or more periodic reports 450.

Figure 5:
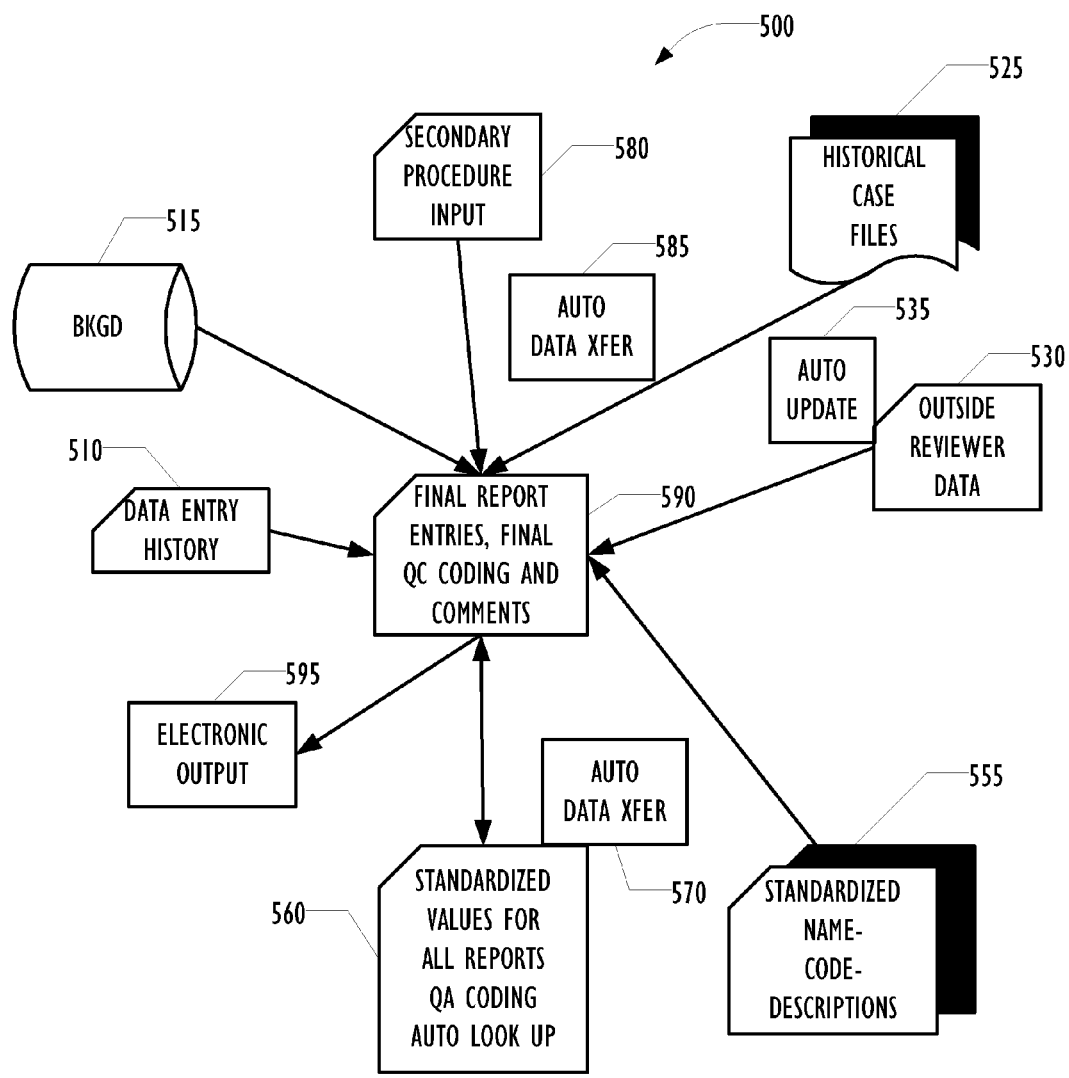
FIG. 5 is a data flow diagram of the generation of final report entries, according to one embodiment of the present invention.

FIG. 5 shows data flow diagram 500 for the generation of final report entries, final quality control coding, and comments 590. Generally, values from the secondary procedure 580 and/or the initial procedure 465 are provided in initializing the final report entries 590. These values are generally provided by auto-update mechanism 585. As shown in previous FIGS. 3 and 4, data entry history 510 and background information 515 may be provided to generate the final report entries 590. Historical case files 525 may also be provided to the final report entries 590. Reviewer data 530 may be provided through an auto-update mechanism 535 to the final report entries 590. As above, standard name-code-description values 555 may also be provided to the final report entries 590, usually based on user indications in commands. Standardized values for all reports, quality assurance coding and auto-lookup values 560 may be provided to the final report entries 590 through an auto-update mechanism 570. Final report entries may be stored as standardized values for all reports 560, as well.

Upon receiving at least an indication of a request for an automatically generated report, the system may be configured to automatically send via electronic output 595 a report with an electronic signature of the person who completed the case. The report is preferably compliant with all regulatory requirements. The electronic interface 595 preferably automatically inserts the fax number of the submitter(s) in the complete case and sends the report to the submitter(s).

The interface is able to determine if the submitter(s) have valid fax numbers that have been approved by them, if the case has been previously faxed, and only fax to the submitter(s) who desire it. If a case has been previously faxed but if for some reason the submitter did not get it, there is an auto override function to allow an immediate fax to be resent.

The interface 595 can be activated by programmed voice macros, keyboard macros, the input device, or execution via an end of day menu routine. It can be applied to the existing case, all of the completed cases, selectively by the user for just the cases completed by the user, or any range of cases.

In addition, notification is sent to all submitters of any case that is being held longer than the standard time that includes the demographic case information, specimen information, date the case was received, and the reason the case is being held. If a case has multiple submitters, each submitter will receive a fax if a valid fax number is on file for that submitter.

Figure 6:
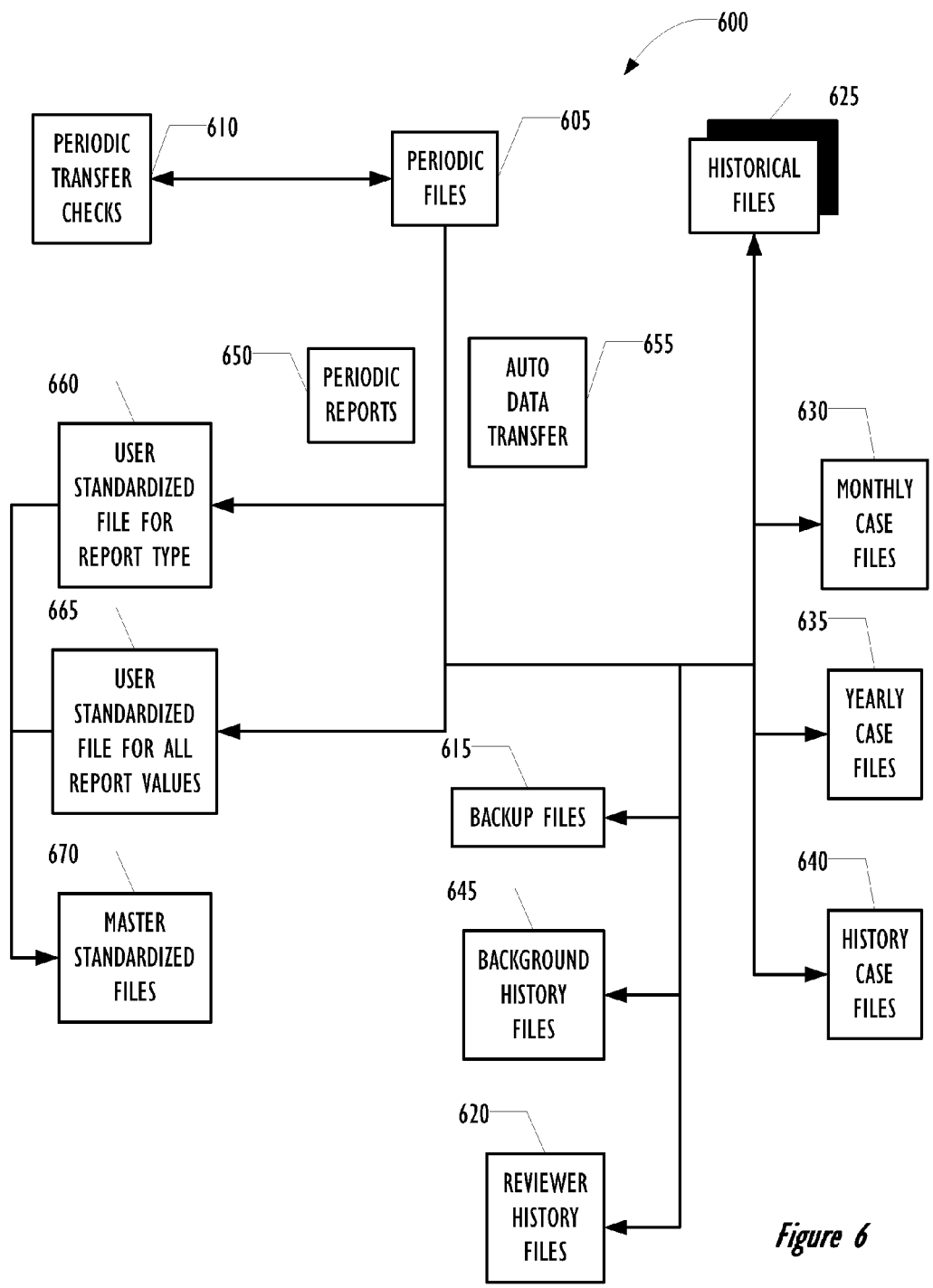
FIG. 6 is a data flow diagram of daily transfers, including daily report generation and backup, according to one embodiment of the present invention.

Turning now to FIG. 6, data flow diagram 600 for periodic transfers is shown, according to one embodiment of the present invention. The periodic transfer checks 610 are exchanged with periodic files 605. The periodic files 605 are used to generate periodic quality management reports 650 and are typically provided through auto-transfer mechanism 655 to the user standardized file for report type 660 as well as to historical files 625. The periodic files 605 are also used to update, typically through auto-transfer mechanism 655, the user standardized files for all report values 665. The user standardized file for report type 660 may also be used to update the master standardized file 670. Historical files 625 may include monthly case files 630, yearly case files 635, and history case files 640. Periodic files 605 and historical files 625 may be provided and stored as backup files 615, background history files 645, and/or reviewer history files 620.

Figure 7:
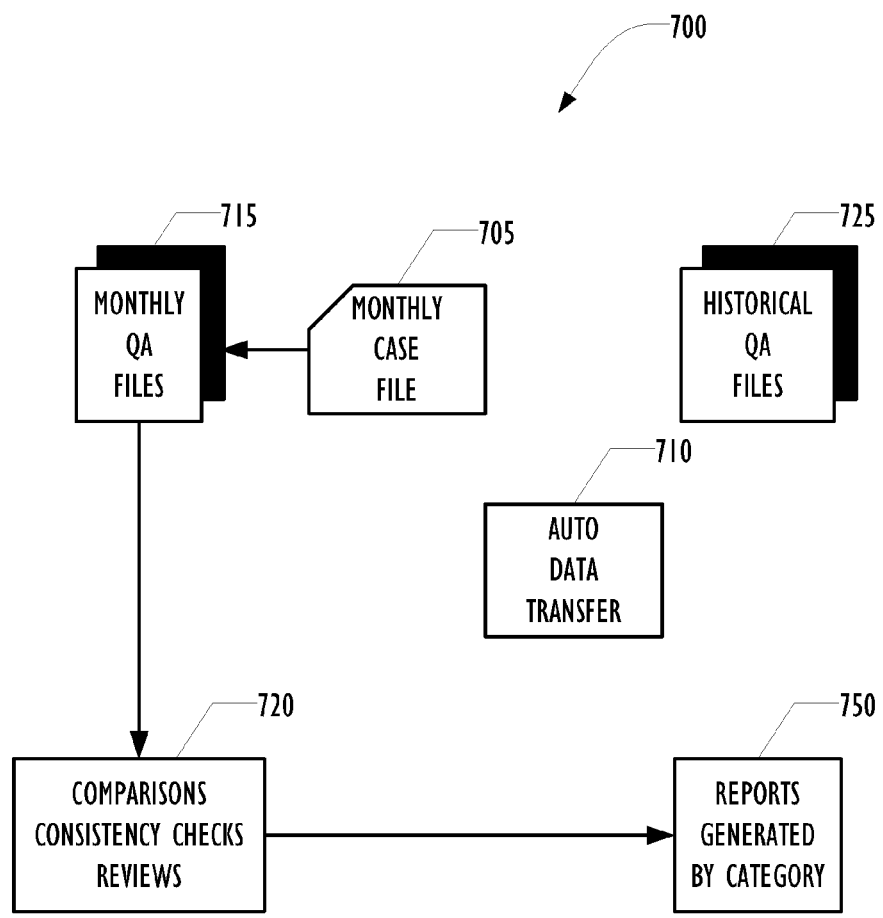
FIG. 7 is a data flow diagram of monthly quality assurance reports generation, according to one embodiment of the present invention.

Turning now to FIG. 7, data flow diagram 700 of quality management report generation is shown, according to one embodiment of the present invention. Data from the monthly case files 705 are included in the monthly quality assurance files 715. The monthly quality assurance files 715 are used to do comparisons, consistency checks, and reviews 720. The historical quality assurance files 725 are typically provided through auto-transfer mechanism 710 along with the comparisons, consistency checks, and reviews 720 to generate reports 750, which may be generated by category. Categories of quality assurance reports that are generated are defined either by the user or by the system. Examples of quality assurance reports include status verification, prediction validation, and user efficiency and/or accuracy/reliability. In various embodiments, a separate report may be generated for each quality management indicator. In other embodiments, reports may be generated based on cross-correlations between or among a plurality of quality management indicators.

Turning now to FIGS. 8-13, a pathology report generation embodiment of the present invention is detailed.

The general process is that in a hospital the pathology labs see all the tissue that goes through the hospital from whatever source. The source may be an operation, a biopsy, or an exam. Whatever the tissue, any specimens taken are sent through the pathology lab. Everything seen in the pathology lab requires a report to be written.

Reports are written at various stages during the examination. For example, an initial examination is recorded for initial specimen sections of the body, slide, etc. The tissue may then be sent off for special studies. Special studies personnel may do their own internal staining or procedures on the specimen sent for special studies. In all cases, they usually prepare cross-sections for microscopic viewing. Once that is done the pathologist will look at the cross-section, and another report will be made. After the second report is made, a diagnosis will be rendered by the pathologist. A diagnosis report will be completed, signed out, and sent to the referring physicians.

Sometimes the report is that the diagnosis is unsure. It may be a difficult case. The case may be sent out for an outside consultation or a consultation for someone to look at it and get a second opinion or a third opinion. If an outside consultation is called for, an additional report will be issued.

In all various stages there are a variety of databases, according to various embodiments of the present invention, that are used to keep track of each of the different reports. As the case progresses through different doctors' offices, the reports may be transferred from one database to the other.

A historical record of a report may be kept in a monthly file, a yearly file, and a historical file. The monthly case file typically has quality control or quality assurance reports run on it. There are a variety of different reports depending on the kind of slide or specimen or particular thing to be examined anywhere from the quality of slides, the quality of the reviews, the quality of the outside consultations. The reports include information such as how long it takes to process cases, the quality of examinations, the quality of initial diagnosis of the practicing physician versus what the pathologist saw. Each set of entries, each template, each report, and each entry of each template is preferably a separate database with the databases linked by unique identifier. The databases and their respective database structures and configurations described herein are exemplary and illustrative and other databases and database structures and configurations can be used as desired, however. For example, a single database consolidated database can be used.

The databases are updated for each new report written, both for completeness and so that the pathologist has a history, daily, monthly, yearly, and personally, for all the reports that are done. Each pathologist has a standard database for each field and there is an individual database for each pathologist. The daily case file may be used by everyone who uses the system. Each pathologist can have a different view of the daily case file. That is, each pathologist can look at the daily case file using the same database but a different screen that identifies the pathologist. Each pathologist can have their own standards files that, when looking up a standard case, use their own standard cases. There is also a master standard file, which contains all standard cases, and if the pathologist encounters a case that is not in the pathologist's standard case file, the pathologist can access the master standard file to determine which case standard file to use.

By dictating data and voice commands, the data are put into the proper field, saved into the database for the particular patient and the particular tissue, whether the examination was a gross or microscopic exam, whether the activity was a diagnosis or a consult, if the diagnosis needs to change, or if there have been a series of examinations. Each diagnosis can generate a particular billing code. The system automatically keeps track of day and time for each entry. Basic demographic data of the patient can be pulled in automatically. Daily reports can be printed automatically. Monthly quality assurance reports can be printed automatically. At the end of the month, the data can be transferred to the appropriate files, the calculations made, the reports printed, all analyses made, and monthly quality assurance reports may even be transferred directly to the hospital so that the hospital knows what the quality assurance parameters are for each pathologist working there.

Billing codes may be automatically generated by the type and number of specimens examined. If any additional procedures, specimen analysis, tests, or special handling of specimens are required during the exam process, the correct billing (CPT) codes are also auto assigned. Each billing code is linked to the specific case and can be printed with case information or electronically transmitted to a billing service or other billing report as necessary. This procedure allows billing codes to be automatically retained with the appropriate case for future review or audit as necessary. In addition, it ensures accurate and timely patient billing while complying with any government mandated billing modifications or limitations. If desired, billing codes can be printed along with a completed case report and electronically transmitted, including auto-faxed, to the appropriate billing address.

Figure 8:
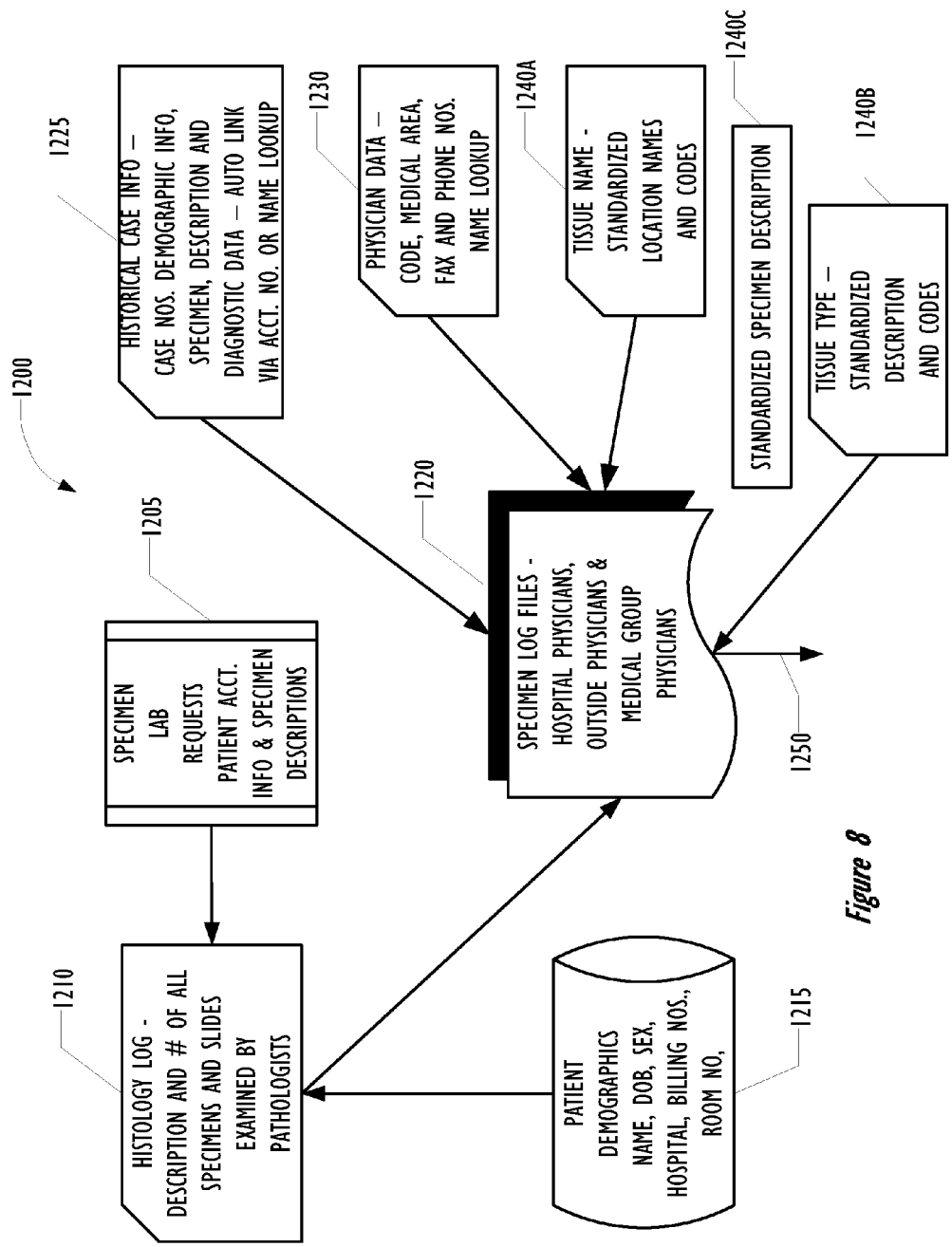
FIG. 8 is a data flow diagram of initial data collection in a pathology report generation embodiment of the present invention.

According to the illustrative pathology report generation embodiment, starting with FIG. 8, the method starts with an initial data collection data flow 1200. A lab specimen request 1205 may include patient account information and specimen descriptions for use by a pathologist. The data in the specimen lab request 1205 are provided to or integrated with a histology log 1210. The histology log 1210 may include description and number of all specimens and slides examined by pathologist within a given group, organization, hospital, etc. Patient demographics 1215 may include name, date of birth, sex, hospital, billing numbers, room number, etc. Patient demographics 1215 are provided to the histology log 1210 and also to the specimen file logs 1220. The specimen files from hospital physicians, outside physicians, and medical group physicians are all within specimen log files 1220.

Historical case information 1225, which may include case numbers, demographic information, specimen, description, and diagnostic data are typically auto-linked up via account number or name look up to the specimen log files 1220. Physician information 1230, which may include code, medical area, and phone numbers, typically by name lookup, is also provided to the specimen log files 1220. Tissue name, standardized location names, and codes 1240A are integrated into the specimen log files 1220, usually by user input commands. Tissue type standardization description and codes 1240B and standardized specimen descriptions 1240C are also integrated into the specimen log files 1220, usually by user input commands.

Slide and specimen preparation and histology logs 1210 may be generated. The initial log automatically retrieves patient demographic information based on a previously assigned patient id hospital number. The log also allows automatic retrieval of previous case history information via the aforementioned hospital id. If an id does not exist, a lookup function is available to examine previous cases by patient name and retrieve the data corresponding to the current patient.

Specimen location and type are entered via lookup to standard anatomic pathologic descriptions that are linked to the appropriate (CPT) billing codes. This log information is transferred to the initial case exam data for the pathologist and saved for further use in histology databases. The number of blocks for each slide is automatically calculated by type of specimen and desired pathology exam slides. Block assignments can be overruled as necessary by the examining pathologist. A link between the completed case examination and the histology log is maintained by means of the automatically generated case number and allows specimen quality info from the completed case to be sent back to the log file for subsequent reporting and review.

Figure 9:
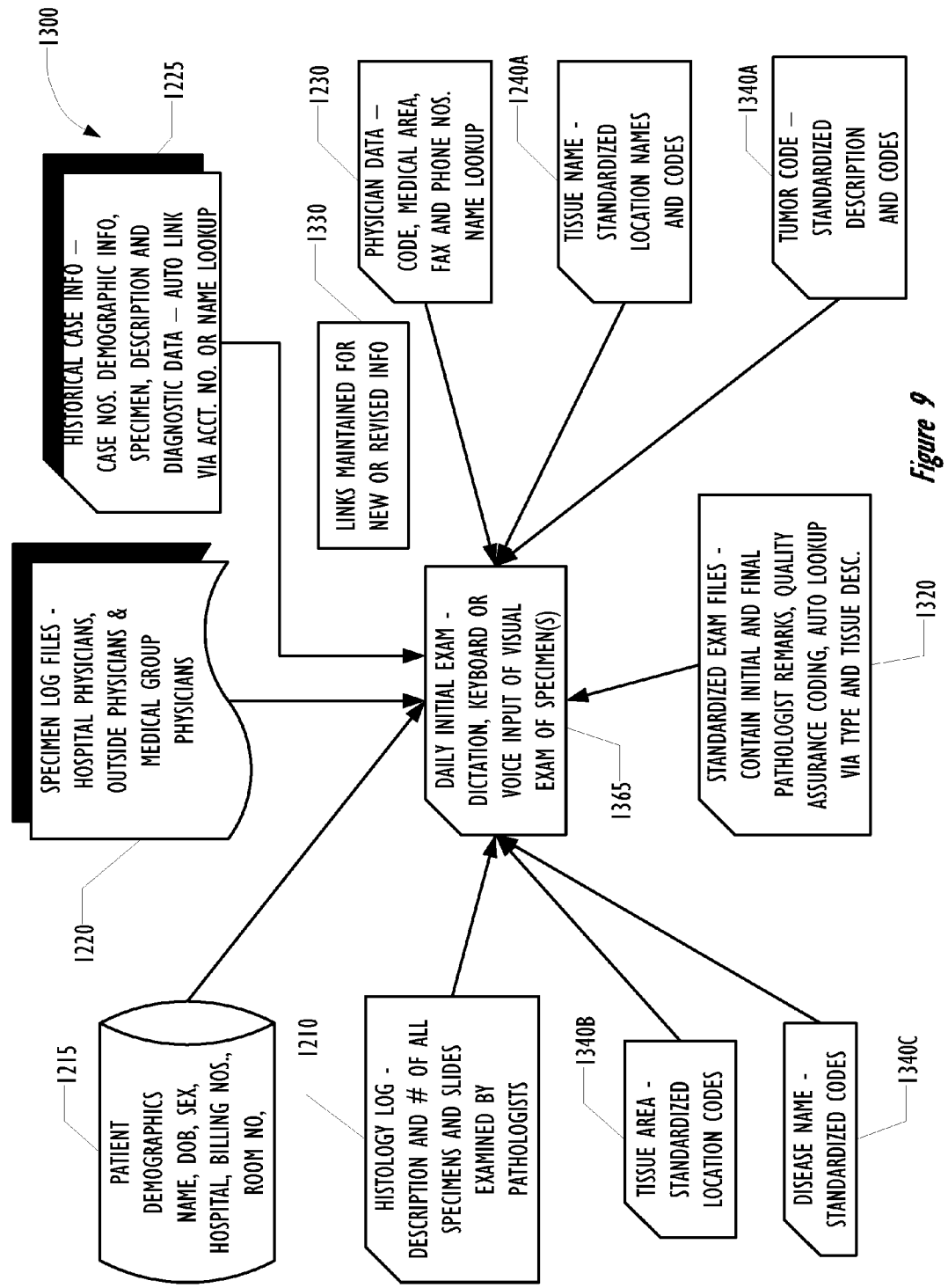
FIG. 9 is a data flow diagram of a pathologist initial exam in a pathology report generation embodiment of the present invention.

Turning now to FIG. 9, a data flow diagram 1300 of a pathologist initial exam of a pathology report generation embodiment according to the present invention is shown. Generation of a daily initial exam 1365 includes the use of input device 110, which may include dictation, keyboard or voice input of visual exams of one or more specimens. The specimen log files 1220 are integrated into the daily initial exam 1365. Patient demographics 1215 may be integrated into the daily initial exam 1365. Histology log 1210 data may also be integrated into the daily initial exam 1365. Historical case information files 1225, physician data 1230, and tissue names 1240A may also be integrated into the daily initial exam 1365. The physician data 1230 is preferably maintained for new and revised information via auto-update mechanism 1330, so that the daily initial exam 1365 is always up-to-date. Tissue area standardized location codes 1340B and disease names standardized codes 1340C may also be integrated into the daily initial exam 1365. Standardized exam files 1320 are integrated into the daily initial exam 1365, preferably by auto-transfer mechanism. Tumor standardized description and billing code files 1340A may be integrated into the daily initial exam 1365. In FIG. 9, integration is preferably by user input command or indication.

Figure 10:
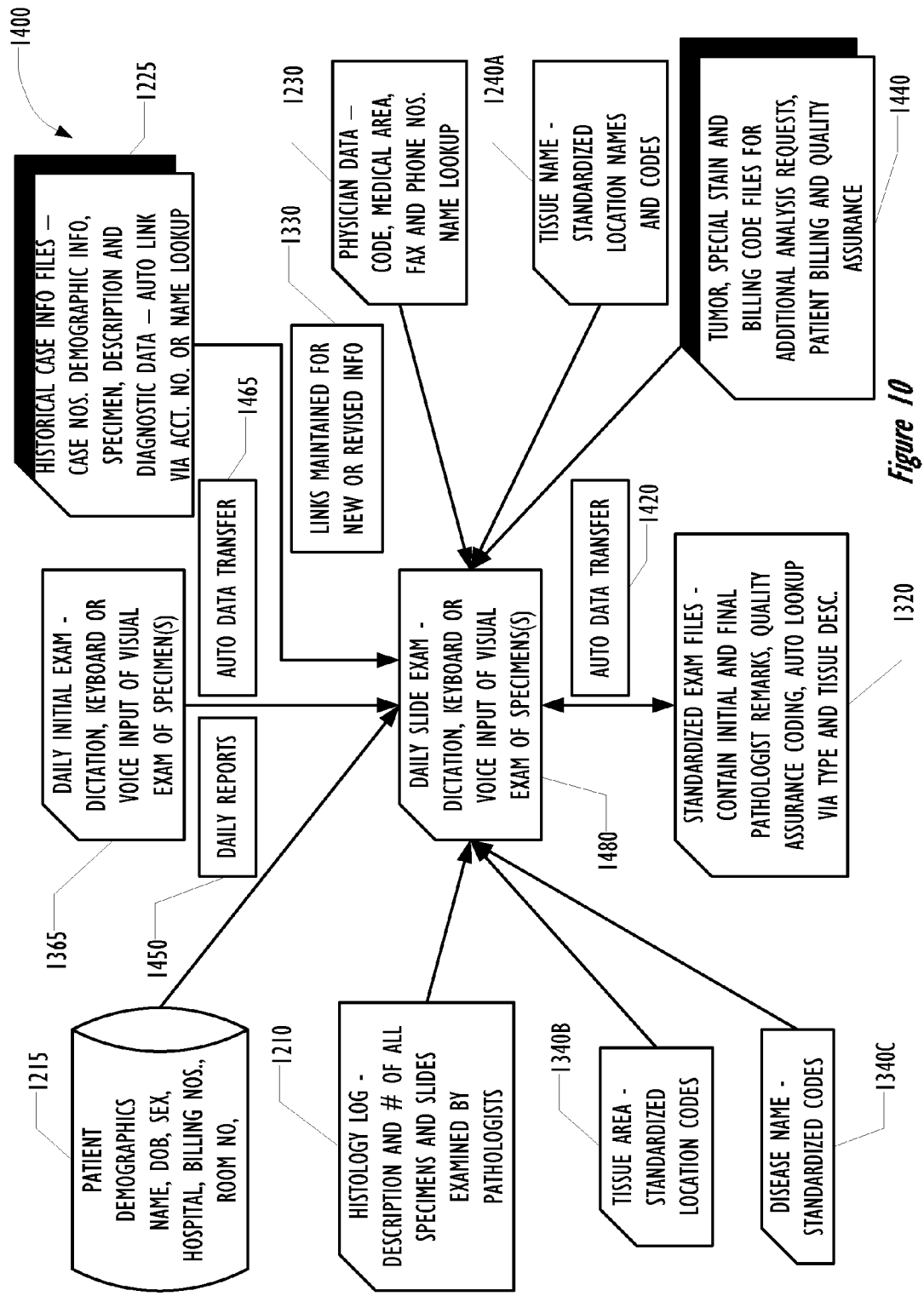
FIG. 10 is a data flow diagram of a pathologist slide exam of a pathology report generation embodiment of the present invention.

Turning now to FIG. 10, a data flow diagram 1400 of a pathologist slide exam of a pathology report generation according to one embodiment of the present invention is shown. Generation of a daily slide exam 1480 includes the user 105 using the input device 110, which may include dictation, keyboard, or voice input, to describe one or more visual exams of one or more specimens. The daily initial exam 1365 is integrated into the daily slide exam 1480. The daily initial exam 1365 is provided to the daily slide exam through auto-transfer mechanism 1465. Patient demographics 1215 are integrated into the daily slide exam 1480. Histology log 1210 may also be integrated into the daily slide exam 1480. Historical case information files 1225, physician data 1230, and tissue names 1240A may also be integrated into the daily slide exam 1480. The physician data 1230 is preferably maintained for new and revised information via auto-update 1330, so that the daily slide exam 1480 always includes up-to-date information. Tissue area standardized location codes 1340B and disease names standardized codes 1340C are also integrated into the daily slide exam 1480, usually by user input codes. Standardized exam files 1320 are integrated into the daily slide exam 1480, usually by auto-data transfer mechanism 1420. Note the daily slide exam 1480 may be reintegrated into the standardized exam files 1320. Tumor, special stain, and billing code files for additional analysis request, patient billing, and quality assurance 1440 are preferably integrated into the daily slide exam 1480.

Figure 11:
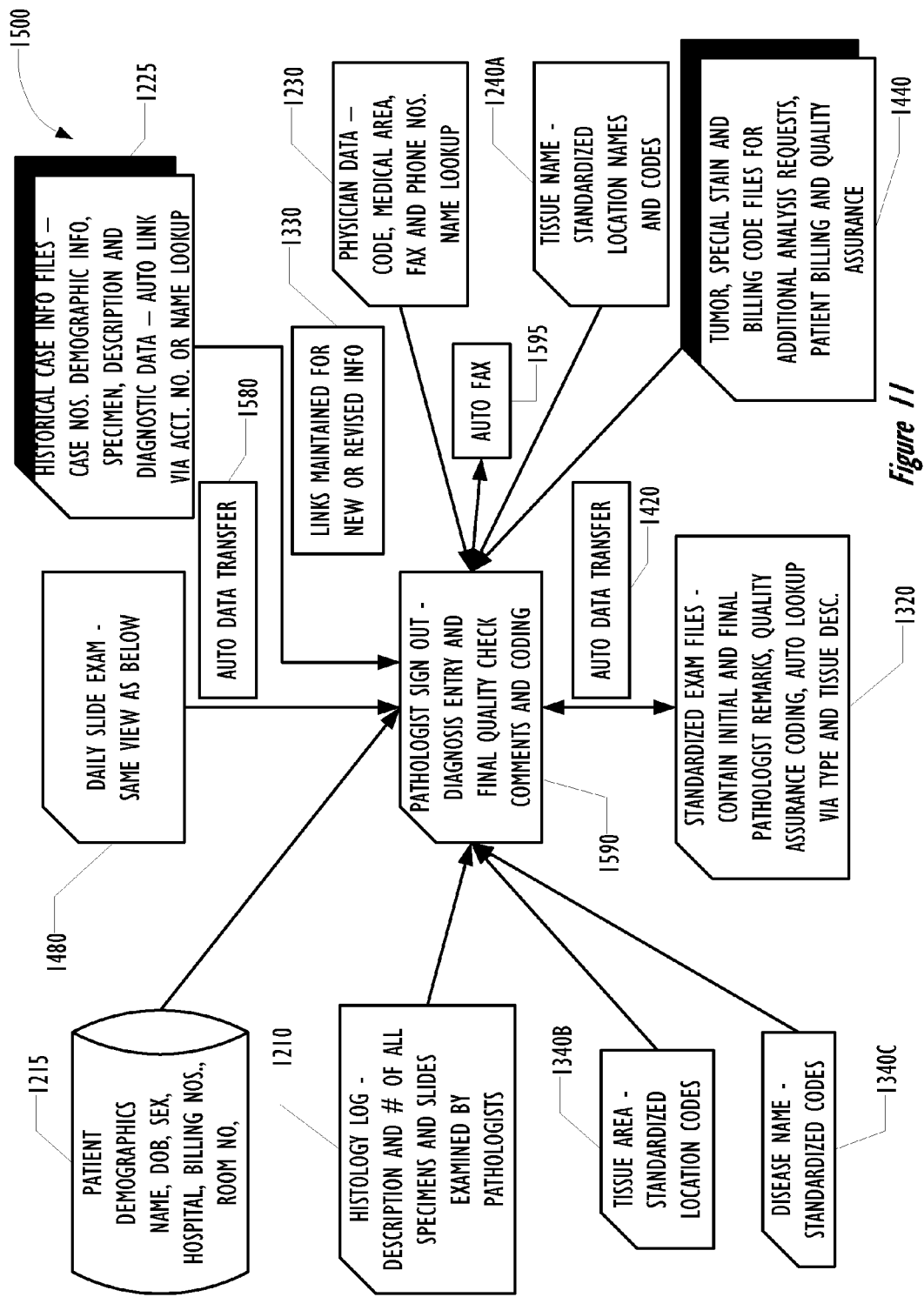
FIG. 11 is a data flow diagram of pathologist sign out of a pathology report generation embodiment of the present invention.

Turning now to FIG. 11, a data flow 1500 of a pathologist sign out of the pathology reports generation according to one embodiment of present invention is shown. The daily slide exam 1480 is provided to the pathologist sign out 1590 by update mechanism 1580. Patient demographics 1215 and histology log 1210 may be integrated into the pathology sign out 1590. Historical case information files 1225, physician data 1230, and tissue name standardization location names and codes 1240A may also be integrated into the pathologist sign out 1590. Physician data is generally updated though auto-update mechanism 1330 for new and revised information, so that pathologist sign out 1590 always has the most up-to-date information. Tissue area standardized location codes 1340B and disease names standardized codes 1340C are also integrated into the pathologist sign out 1590, usually by user input codes. Tumor, special stain, and billing code files 1440 are also typically integrated into pathologist sign out 1590 by command codes. Standardized exam files 1320 are auto-transferred through auto-update mechanism 1420 to the pathologist sign out 1590. The pathologist sign out 1590 values may be reintegrated into the standardized exam files 1320. Pathologist sign out 1590 should include the diagnosis entry and final quality check comments and coding.

Upon receiving at least an indication of a request for an automatically generated report, the system may be configured to automatically send via facsimile output 595 a case report with an electronic signature of the pathologist who has complete the case diagnosis. The report is preferably compliant with all regulatory requirements, such as HIPAA. The facsimile interface automatically inserts the fax number of the submitting physician(s) in the complete case and sends the report to the submitting physician(s).

The interface is able to determine if the submitting physician(s) have valid fax numbers that have been approved by them, if the case has been previously faxed and only fax to the physician(s) who desire it. If a case has been previously faxed but if for some reason the physician did not get it, there is an auto override function to allow an immediate fax to be resent.

The interface can be activated by programmed voice macros, keyboard macros, the input device, or execution via an end of day menu routine. It can be applied to the existing case, all of the completed cases, or selectively by the pathologist for just the cases completed by him or her. Users can automatically select their own reports or all completed reports for faxing.

In addition, notification is sent to all submitting physicians of any case that is being held longer than the standard time that includes the demographic case information, specimen information, date the case was received, and the reason the case is being held. If a case has multiple submitting physicians, each physician will receive a fax if a valid fax number is on file for that person. Held cases that have been faxed are flagged to prevent multiple transmission of the same case until completion. If necessary, cases can be retransmitted, upon request to any additional attending physicians or to the original ones. The transmission is accomplished by calculated links between the attending physician(s) for the case, a separate data file containing the transmission routing info, and programmed links built into the reports to communicate the proper dialing and/or routing instructions to the fax server or other electronic service.

Figure 12:
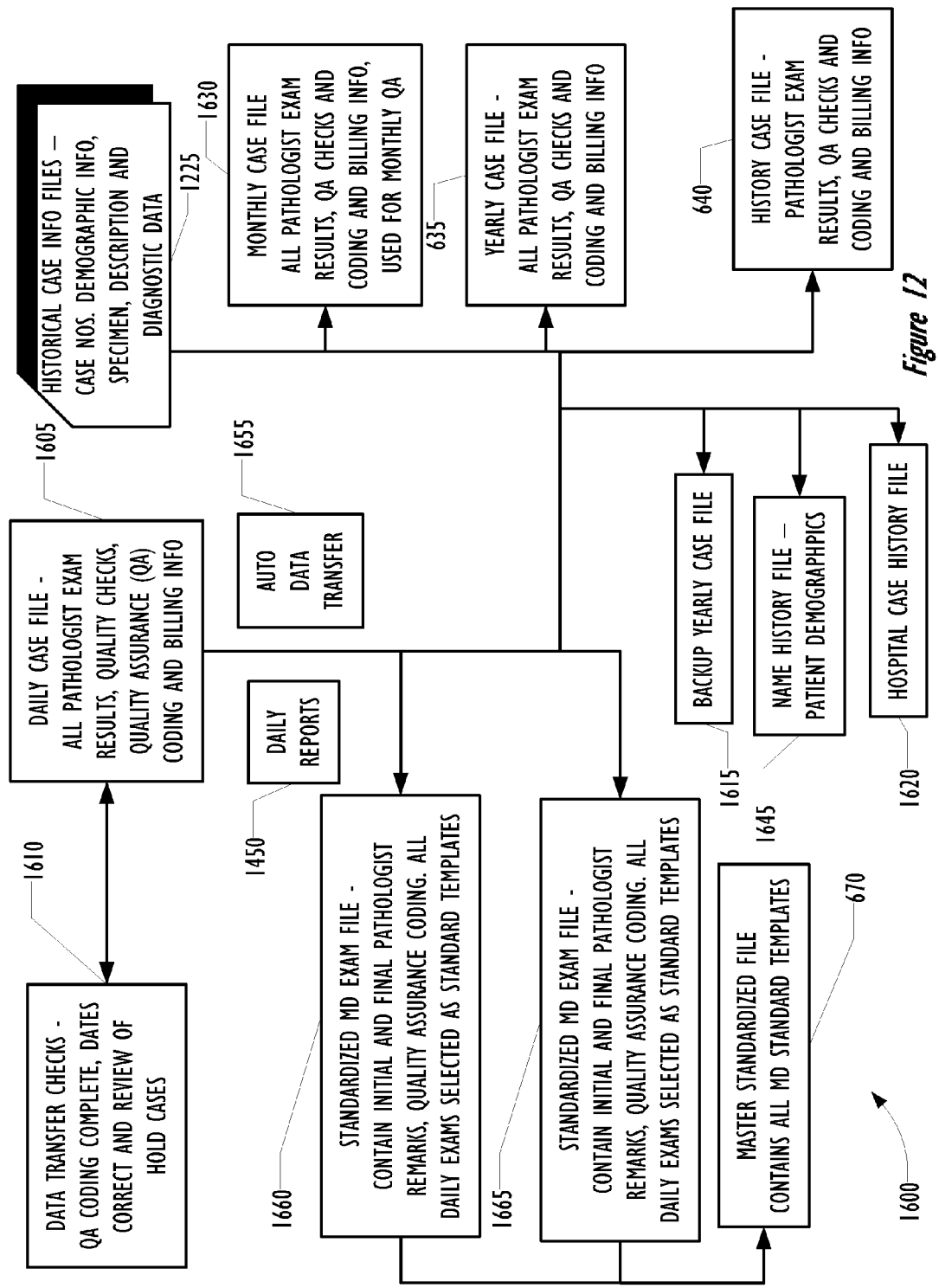
FIG. 12 is a data flow diagram of daily transfer made in a pathology report generation embodiment of the present invention.

Turning now to FIG. 12, data flow diagram 1600 of daily transfers for quality assurance purposes is shown. Daily case files 1605 generally include all pathologist exam results, quality checks, quality assurance coding, and billing information. Data transfer checks 1610 are performed by a computing engine to check to see that quality assurance coding is complete, the dates are correct, and reviewing for completion all cases that have been held at the pathologist's request. The daily case file 1605 exchanges data with the data transfer checks database 1610. Daily reports 1450 may be generated automatically from the daily case files 1605 through auto-update mechanism 1655. The daily case files 1605 are provided to and update the standardized physician's exam file 1660. The standardized physician's exam file 1660 may contain initial and final pathologist remarks, and quality assurance coding. All daily case files may be converted to a standard template for future exams, for addition to standardized physical exam file 1660. Note that the daily case file information 1605 may also be provided to a standard backup standardized physician's exam file 1665.

Standardized physician exam file 1660 may also be used to update the master standardized exam file 1670, which contains all the physician's standard templates. The daily case file 1605 is provided and integrated into the historical case information files 1225, including one or more of the monthly case files 1630, the yearly case files 1635, and the history case files 1640. Each of the monthly case files 1630 includes all pathologist exam results, quality assurance checks and coding and billing information for a month's time. The monthly case files 1630 are used for monthly quality assurance reports. Each of the yearly case files 1635 includes all pathologist exam results, quality assurance checks and coding and billing information for a year's time. The history case file 1640 includes all of the pathologist exam results across all times periods, all quality assurance checks, and all coding and billing information. There can be a backup yearly case file 1615, which is maintained for backup purposes. There can also be a name history file with patient demographics 1645, which is maintained across all patients. A hospital case history file 1620 may be updated for all cases for a given hospital.

Figure 13:
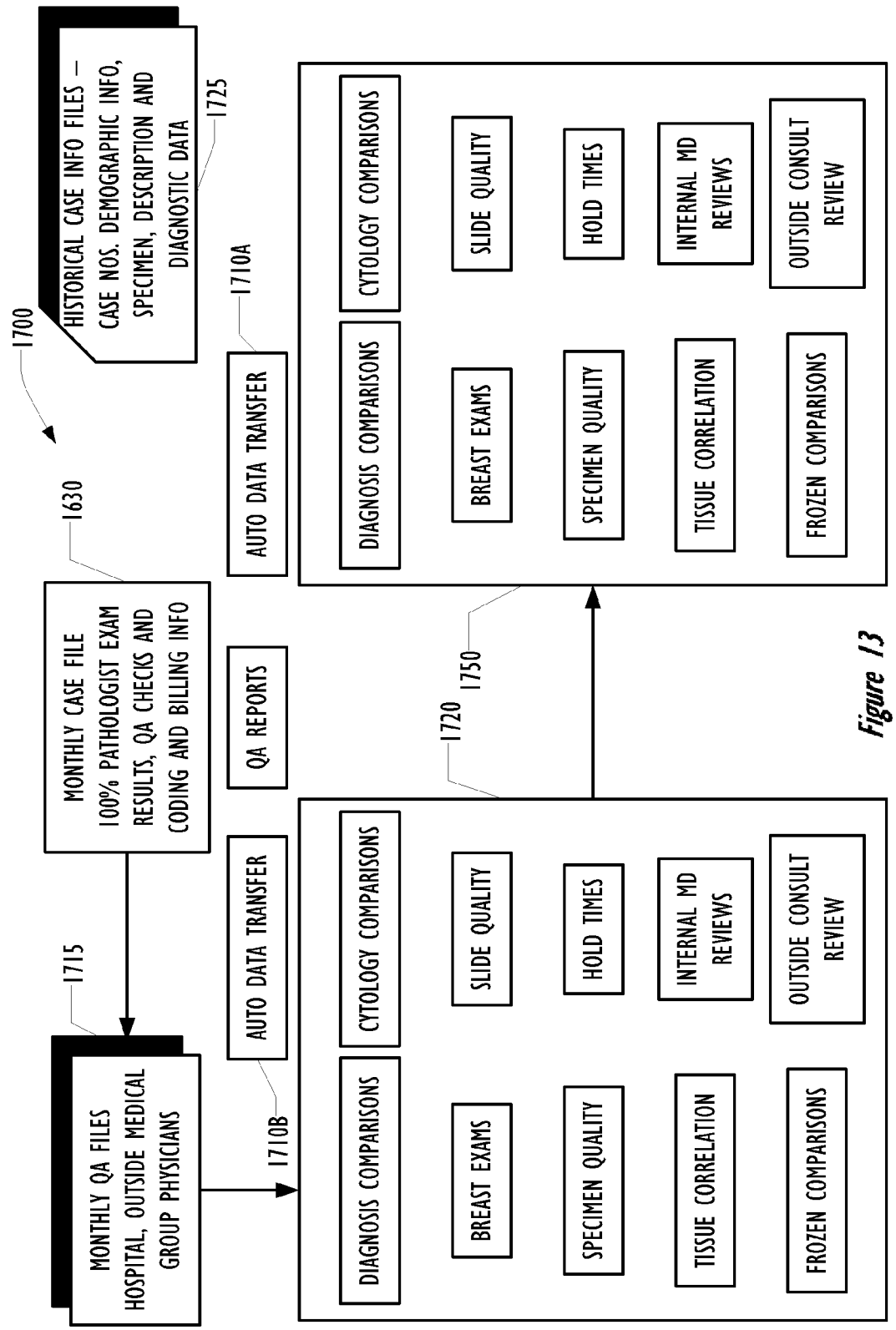
FIG. 13 is a data flow diagram of quality assurance reports generated in a pathology report embodiment of the present invention.

Now turning to FIG. 13, data flow diagram 1700 is shown, where quality assurance reports are generated for the pathology report generation embodiment of the present invention. The monthly case files 1630 are integrated into the monthly quality assurance files for the hospital, outside medical group, physician, etc. 1715. The values are preferably transferred using auto-update transfer mechanism 1710B. The monthly case file 1630 is also integrated into the historical quality assurance files for the hospital, the outside medical group, the physicians, etc. 1725 using auto-data transfer mechanism 1710A. The monthly quality assurance file 1715 may include one or more of the following groups shown at 1720: diagnosis comparisons, breast exams, specimen quality, tissue correlation, frozen comparisons, cytology comparisons, slide quality, hold times, internal physician reviews, and/or outside consultant reviews. These groups are exemplary and illustrative only and other groups could be included. The monthly quality assurance files 1715, including subsets in 1720, are used to generate quality assurance reports 1715 for any one or more of the subsets including diagnosis comparisons, breast exams, specimen quality, tissue correlation, frozen comparisons, cytology comparisons, slide quality, hold times, internal physician reviews, and/or outside consultant reviews. These quality assurance reports are exemplary and illustrative only and other reports could be generated as desired.

According to various aspects of the present invention, the pathologist is able to input data on the spot, when the observation is made. The pathologist is allowed to input the data for a particular case, so it is prospective, and the system can create reports at the end of the day, at the end of the month, or whenever, which become the basis of quality assurance on any anatomic pathology specimen that comes through the hospital or laboratory. The College of American Pathology (CAP) requires that ten percent of all cases be reviewed, but does not mandate which ten percent or how to review the ten percent. CAP requires that the reviewer say what cases were reviewed and how they compare to usual expectations. If the cases reviewed do not match the usual expectations, then the report must explain why they did not match those usual expectations and whether there was a major effect on the patient.

When quality assurance is performed retrospectively, a lot of data is skipped. It is very difficult to go through materials retrospectively and pull information out that is usable for improving quality performance of a pathology system. Retrospective reviews only pull out a very small fraction of the cases, representing a fraction of the work performed. According to various embodiments of the present invention, up to 100 percent of the cases performed up to 100 percent of the time can be reviewed on a prospective, ongoing basis. In one embodiment, greater than 90% of all cases are reviewed.

Histology is the preparation of slides and the preparation of materials. A pathologist takes a wet tissue, like breast tissue, for example, takes a slice of the tissue, and then puts the tissue through a process where it comes out on a glass slide. The tissue is then examined under a microscope. During the preparation from wet tissue to glass slide, a staining process is performed. One quality assurance report that is needed is the quality of the staining process.

In performing a daily initial exam 1365, or a daily slide exam 1480, or pathologist sign out 1590, the user 105, here a pathologist, will call up a standard template for the particular report being filled out. The template may be from the pathologist's personal collection of templates or it could be retrieved from a database of standard templates. Navigation from entry to entry in the template is by voice command, or other command, through the input device 110 shown in FIG. 1A. In one embodiment of the present invention, new entry locations are made in the middle of the report, with set entry locations at the beginning and the end of the report being unchangeable.

As an example of observations using both data and commands, consider a gross examination of a tissue. A voice command identifying that a gross examination was occurring would pull in the template for gross examination. A second voice command can indicate a multiple biopsy such as stomach biopsy and rectum biopsy. The voice command pulls in entry field data for the descriptions required for gross examinations for multiple biopsies for stomach and for rectum based on the data and commands given. If the stomach showed chronic gastritis or mild chronic gastritis, for example, then the database system macro will pull in the required description based on what is essentially a voice shortcut and also input those additional entries that need to be made. If the rectum has a polyp, for example, and there is no rectum polyp standardized template but there is a colon polyp, then the colon polyp template can be called up, modified, and saved as a macro for rectal polyps.

Database entries may include billing codes as well. Files, reports, or other entries can automatically import billing codes in response to values of data put in reports and/or commands within the data put in the reports. As an example of a quality assurance mechanism that can be automatically applied to a report without additional input required by the pathologist or the user, consider a pathology report where no patient history is supplied. The quality assurance report for the day, for the month, for the year or for any history value for a given pathologist group or hospital, will automatically highlight an entry with no patient history provided.

Quality assurance data can be filled in individually, can be filled in automatically by the computing engine, or can be automatically supplied such as time stamps on when reports were started, finished, etc. Consider also a case where the cytology needs to be compared with tissue that will arrive later. A quality management report can indicate whether the cytology report and the tissue biopsy agree. If there is an outside consultation and the case is sent elsewhere, the quality management report can indicate whether the outside consult agreed with the diagnosis made by the original pathologist. If a frozen section is compared with a diagnosis that occurs later, or with the initial look at a later frozen tissue to determine whether the frozen tissues match the diagnosis, a quality management report can indicate whether there was agreement. In another example, CAP requires a cytosource and cytotype data, to allow a report of, for example, how many slides were read by the pathologist for non-gynecological cytologies. Pathologists are typically limited to a maximum of 100 cytology slides a day. The daily reports determine exactly how many slides were read by the pathologist.

The following is a specific embodiment of the present invention for generating pathology reports with statistical report follow-up on at least daily and monthly bases. The overall methodology insures reporting accuracy and quality. Extensive use is made of standardized case templates and master patient and physician data files to ensure consistent and repeatable reporting of case exams. There is a 100% quality assurance review of all pathologist exams in relational databases since 1990 allowing rapid and extensive reporting and analysis of cases. Data redundancy is ensured using routine daily backups to multiple locations, backups of data during significant daily operations including data transfer from different file structures, and multiple files of the same data. The multiple files include monthly, yearly, and historical archives and they are used not only as backups but also as sources of data for daily, monthly, and yearly quality assurance and statistical analysis. All daily cases are printed and faxed or delivered to attending physician(s) upon completion. In addition, cases may be printed by a specific case, by a group practice, specific physician, staff, pathologist, or secretary, specific date or range of dates from the current or previous year(s) and the number of copies of the exam can be varied depending on the desires of the group practice or attending physicians.

Efficiency of operation is ensured by allowing for both keyboard and voice input availability for data entry, navigational commands, data lookups, and selection of fields and/or records. There is extensive use of macros, both keyboard and voice, to perform data retrieval, lookups, print requests, field calculations, and searches, etc. Standardized exam reports can be instantly retrieved into exam fields without retyping or requiring the user to copy and paste text from a file. Single entry of data combined with automatic transfer of data from a single source to multiple different file structures with identical field names. Automatic data retrieval is based on matching field information from exam and master files. Field calculations are based on already entered exam data and/or standard values.

Manual lookup of information from large master files such as patient demographic information is used to retrieve unknown case info. As first character is entered or spoken, the corresponding value is nearly instantaneously (even with hundreds of thousands or more records in the master file) displayed from the master file. As succeeding characters are entered, the search is further refined until the desired information is found. Multiple records from the master file are displayed simultaneously and the page and cursor keys can be utilized or voice activated at any time to select the desired record. The desired information from the master file is then automatically inserted in the exam file. The lookup info, e.g., name, does not have to be the value placed in the exam field. A code such as patient no. for that patient can be the value retrieved and then that code would be the basis for automatic retrieval of the other pertinent information from the master file without performing a lookup. Select fields have only a limited number of acceptable values, e.g. the pathologist's name. When the data entry area of these fields are reached, the acceptable values will display (popup) on the screen and only one of those values can be selected.

Completed records are transferred daily from each file in succession. Daily log data are retained in the log files. The transfer is based on a date range, but normally it is the current date. All gross information is transferred daily to the case exam file, the information backed up, and then deleted awaiting new information from the log file(s). Daily case exam and monthly completed case reports await monthly quality assurance reports and analysis. Yearly completed case reports are produced either automatically or on demand. There is a historical archive of all cases. Completed cases are transferred daily from the case exam file to the monthly, yearly and archive files. Upon successful completion of the daily transfer, a backup of the daily file is made and the completed case information is deleted from the daily file leaving the cases on hold until additional information or reviews are completed.

Description of patient files includes patient demographic data transferred from Hospital (or clinic, etc.) files, including name, hospital number, patient number, age, date of birth and date in hospital.

Patient log data is created including the following information: case number and exam date, demographic data using auto lookups based on patient number used to access demographic file and retrieval information. The attending physician(s) information includes manual lookup of name from physician file, diagnosis code auto retrieval, origin code (physician practice location, e.g., surgery, OB-GYN, endoscopy, etc.) auto retrieval, and facsimile number auto retrieval. Case information includes the number of frozen slides, type, source and number of cytology slides, previous exam case numbers for the same patient contained in the historical archives, with manual lookups by patient name and date of birth used to match individuals and retrieve the appropriate case numbers, and cytology data (if any). The cytology data includes the type of specimen (e.g., csf, fluid, sputum, etc.), the source of tissue or substance (e.g., kidney, lung, liver, etc.), and the number of slides. Specimen(s) information, e.g., for up to twelve (or other number as desired) specimens, includes: source of tissue or substance (e.g., kidney, chest, etc.) with information retrieved from the master tissue name file to ensure standardized reporting and accuracy, location using free text based on actual specimen, type of specimen (e.g., washing, biopsy, fluid, segment, etc.), and the specimen description is an automatic calculation based on other entries.

The gross exam file includes all data transferred from the log file plus results of the pathologist's initial visual exam of patient tissue or substance submitted by attending physician(s). Patient case information from the archive case number(s) entered above is automatically printed and made available for the examining pathologist. Upon completion of the initial exam of the daily cases transferred from the log file, each case's information is transferred to the daily exam file. Once the case records are transferred and a backup copy is created, the information is deleted and the file is ready for the next transfer from the log files. Gross exam file information includes log information, gross exam results based on the pathologist's visual exam of material, any lookup value(s) for standardized case information (if any), which allows rapid entry of all repeated information from similar previous cases, pre and post operative diagnosis of attending physician(s), standardized (if available) tissue and disease codes, and the name of examining pathologist.

The daily exam file includes all data transferred from the gross exam file plus results of the pathologist's microscopic exam of the slides, case diagnosis, quality assurance review data, and completed case information. A variety of field types are utilized to help ensure accurate and complete evaluation of patient exam and expedited data entry. These types include mandatory entry/error check, restricted entry, calculated and lookup fields as described in the following overview. The daily exam file includes log information, gross exam results, the report of the pathologist's microscopic exam of slides, the pathologist's case diagnosis, mandatory error check entry fields, restricted entry fields, calculated fields, lookup fields, and quality assurance fields.

Mandatory error check entry fields require information in these fields before the exam can be saved or transferred. Data in these fields are necessary for proper reporting of the exam results and quality assurance analysis. The mandatory error check entry fields in this embodiment are: "std"—transfer case information to standardized case file—y or n; "and"—addendum case—y or n; "cty"—cytology fluid type; "cs"—cytology fluid source; "#cs"—number of cytology slides; "rev"—pathologist review info. Exam results will not transfer without an entry in this field. "arev"—status of review above; "origin of specimen"—medical area of attending physician; "sentln"—presence of sentinental lymph node in specimen—y or n; "report date"—completion date of pathologist's exam (results will not transfer without an entry in this field). "Hold"—case complete—y or n (exam must not be on hold to transfer); and "Rhold"—reason for hold (exam will not transfer without a value in this field and if case has been on hold longer than three days, it must have a value other than a no hold status).

Restricted entry fields are entry limited to only selections displayed on screen when that field is selected.

Table of Restricted Entry Fields and associated options for each field. The values in this table are exemplary and illustrative only.

| Restricted Entry Field Name | Options for Restricted Field |
|---|---|
| bc—bullet case-indicator of text to stay on single line of text | n—standard layout, no bulleted text, g—gross and diagnosis entry form 80 column text, ctrl F8 to access |
| and—indicator of an addendum case with additional information | n—Not an Addendum Case y—Addendum Case |
| sentln—indicator that case was sent for sentinel lymph node testing | N—No Sentinal Lymph Node Y—Sentinal Lymph Node present in specimen |
| tissue cd1—tissue status | A—Abnormal D— |

-continued

| Restricted Entry Field Name | Options for Restricted Field |
|---|---|
| | N—No Atypical Features |
| | F—Fibrous Adhesions/Fibrous Obliteration |
| slide code—acceptable or problems | 01—Acceptable slide |
| | 00—No slide |
| | 02—Air under coverslip |
| | 03—Permount under slide |
| | 04—Irregular staining |
| | 05—Fragmented section |
| | 06—Labeling problem |
| | 07—Overstained |
| | 08—Incomplete section |
| | 09—Embedding problem |
| | 10—Processing problem |
| | 11—Special stain unacceptable |
| | 12—Insufficient Material |
| | 13—Other |
| aslide—action to take if slide problem | 01—accepted |
| | 00—redone |
| prematch—description of pathologist and clinical correlation | 01—Yes, Pre DX match. |
| | 02—Unknown Pre DX |
| | 03—Pre DX differs. |
| | 04—Unsuspected path findings. |
| | 05—Irrelevant Pre DX. |
| | 06—SIMV/Other. |
| | 07—Verbal Match. |
| | 08—Verbal Disagree. |
| sc—Specimen Code-describing adequacy of specimen | 00 = ADEQUATE |
| | 01 = IMPROPER LABEL |
| | 02 = IMPROPER FIXATION |
| | 03 = MORE THAN ONE SPECIMEN IN ONE CONTAINER |
| | 04 = NO TISSUE |
| | 05 = INSUFFICIENT MATERIAL ON SLIDE |
| | 06 = TYPE OF ANESTHESIA NOT NOTED |
| | 07 = INSUFFICIENT SPECIMEN |
| | 08 = IMPROPER REQUISITION |
| | 09 = ADEQUATE BUT INSUFFICIENT |
| | 10 = INCORRECT SPECIMEN |
| | 11 = CONTAMINATED SPECIMEN |
| cs—Cytology Fluid source | nn none |
| | bl bladder |
| | kd kidney |
| | bt breast |
| | lg lung |
| | ty thyroid |
| | lv liver |
| | bn bone |
| | ln lymph node |
| | st soft tissue |
| | sp cerebral spinal fluid |
| | ov ovary |
| | ur urine |
| | pl pleura |
| | ac abdominal cavity |
| | jt joint |
| | pr pericardial |
| | oo other organs |
| cty—Cytology Fluid Source | nn none |
| | ur urine |
| | bw bronchial washings |
| | pf pleural fluid |
| | csf csf |
| | bp FNA/TNB |
| | ba breast aspiration |
| | of ovarian fluid |
| | brs brushings/smear |
| | sm sputum |
| | ot other |
| c#s—Number of cytology slides | count value |
| cytomtch—correlation of cytology and specimen data | 00—No cytology |
| | 01—match |
| | 02—No match |
| | 03—Other |
| acyto | 01—None |
| | 02—Notify Physician |
| | 03—Addendum report |
| | 04—Review by Pathologist |
| | 05—CME |
| | 06—GF |

-continued

| Restricted Entry Field Name | Options for Restricted Field |
|---|---|
| Pathologist | M. Rundell |
| | J. Smith |
| | L. Jones |
| | E. Yang |
| sec—case typist's initials (with dictation often the pathologist) | mr |
| | js |
| | lj |
| | ey |
| | std |
| | sc1 |
| | sc2 |
| | sc3 |
| | new |
| | temp |
| | blank |
| page | 1—last page |
| | blank |
| sqa—secretary quality assurance | Y—Case typed correctly |
| | G—Grammar errors |
| | C—Coding errors |
| | I—Information incorrect |
| | O—Missing data |
| | S—Spelling errors |
| reviewer | NO—Blank |
| | EY—Dr. Yang |
| | MR—Dr. Rundell |
| | JS—Dr. Smith |
| | LJ—Dr. Jones |
| | YS—Drs. Yang and Smith |
| | YJ—Drs. Yang and Jones |
| | RS—Drs. Rundell and Smith |
| | SJ—Drs. Smith and Jones |
| | RY—Drs. Rundell and Yang |
| | RJ—Drs. Rundell and Jones |
| | XY—Random Dr. Yang |
| | XR—Random Dr. Rundell |
| | XS—Random Dr. Smith |
| | XJ—Random Dr. Jones |
| arev | 00—No Review |
| | 01—Consensus Diagnosis |
| | 02—Consensus - Addendum Report |
| | 03—Consensus - Outside Consultant |
| | 04—Consensus - Review of similar cases |
| | 05—CME |
| | 06—Non Consensus - Outside Consultant |
| | 07—Non Consensus-Review Literature & Develop Consensus Diagnosis |
| outside consultant | 01—No Outside Consultant used |
| | 02—outside Consultant agreement |
| | 03—Consultant differential agreement |
| | 04—Consultant diagnosis disagreement |
| | 05—Other |
| aout—reason for being sent out | 00—No Outside Consultant |
| | 01—None |
| | 02—Addendum Report |
| | 03—Additional outside consultant |
| | 04—Auto review of similar cases |
| | 05—CME |
| | 06—GF |
| sentout—where sent for outside consultation | NONE—None |
| | MDA—M D Anderson |
| | DR. HENRY—Dr. Page |
| | DR. RICHARD—Dr. Richard |
| | DR. DAVID—Dr. David |
| | PROPATH—Propath |
| | MAYO—Mayo Clinic |
| | TCH—Texas Children's Hospital |
| | BAYLOR—Baylor College of Medicine |
| | OTHER—Other |
| frozen—evaluation of frozen specimen(s) | 00—No Frozen |
| | 01—Frozen dx matches final dx |
| | 02—Difference in wording |
| | 03—Focal lesion |
| | 04—Uniformly deferred |
| | 05—Deferred, differential |
| | 06—Failure to identify lesion grossly |
| | 07—Sampling problem |
| | 08—Sectioning problem |

| Restricted Entry Field Name | Options for Restricted Field |
|---|---|
| | 09—Staining problem |
| | 10—Interpretation problem |
| | 11—Labeling problem |
| | 12—Communication problem |
| | 13—Other |
| afxmatch—action to take if problem with frozen specimen | 01—None |
| | 02—Notify Physician |
| | 03—Addendum Report |
| | 04—Review of all similar cases |
| | 05—CME |
| | 06—GF |
| rfd—reason for delay, if any | N—No Delay |
| | U—Unscheduled Case |
| | C—Schedule Conflict |
| | L—MD Late Response |
| | T—No Action |
| afd—action to take after delay, if any | N—None |
| | C—Schedule Coordination Review |
| | S—Staff Training |
| | T—Pathologist Training |
| | _—No Action |
| fmm—description of evaluation of frozen specimen and diagnosis, if any | N—No Frozen or No Diagnosis Differences |
| | M—Minor Frozen Diagnosis Difference |
| | Y—Major Frozen Diagnosis Difference |
| mam—source of breast material, if any | N—No Breast |
| | C—Core Biopsy by Radiologist |
| | S—Core Biopsy by Surgeon |
| | X—Excisional Biopsy |
| | M—Mastectomy Specimen |
| | L—Needle Localization |
| | O—Other |
| premam—initial breast diagnosis, if any | N—No breast |
| | C—Calcification |
| | M—Mass Lesion |
| | A—Arch. Dist. |
| | S—Asymmetrical Density |
| | D—No Diagnosis |
| ms—initial suspicion of breast cancer, if any | 0—No Breast |
| | 1—Very Low Suspicion |
| | 2—Low Suspicion |
| | 3—Moderate Suspicion |
| | 4—Suspicion |
| | 5—High Suspicion |
| mammat—correlation of pathologist's exam and clinical impression | 00—No Breast |
| | 01—Breast, No Info |
| | 02—Breast, Match |
| | 03—Breast, No Match |
| sm/basc—locality indicator for cases referred to the pathologist | _—blank |
| | BASC |
| | DSC |
| | SM |
| hr—indicator if special processing is required | n—No Special Processing |
| | y—Special Stains Required |
| | _—Blank |
| ha—action to be taken for follow-up, if any | n—No Action |
| | r—Recut |
| | d—Deeper |
| | s—Step sections |
| hold | N—No Hold |
| | H—Hold |
| rhold—reason for hold, if any | N—No hold |
| | B—Sentinel Lymph Node Clearing |
| | C—Outside Consultant |
| | D—Decalcification |
| | E—ER/PR |
| | K—Fixation |
| | L—Lymph Node Clearing |
| | P—Physician Review (may be specific or random) |
| | S—Special Stain |
| | T—More Tissue |
| | X—Additional Sections |
| | O—Computer down time |
| ahold—action to be taken after hold, if any | 00—No Hold |
| | 01—No Action |
| | 02—Notify pathologist |
| | 03—Notify physician |
| | 04—Notify histology |
| | 05—Notify service |

| Restricted Entry Field Name | Options for Restricted Field |
| --- | --- |
| | 06—Notify consultant |
| | 07—Monitor |
| | 08—GF |

Calculated Fields have field values are based on values from other fields in the same file or values from other linked files. No manual data entry is allowed as the desired information is automatically entered. Default equations can be specified for a field, but they are only suggested values. The value is automatically inserted only if there is no data currently in the field. It can be overwritten by the operator if desired. Exemplary calculated fields and corresponding default equations are as follows:

aa. mamact—breast action field
if[mammat]="01" or [mammat]="03"
then "01" else "00"

bb. type—Source of patient case, i.e., S, P, B or G and is determined at initial entry in appropriate log file.
left([case no],1)

cc. prntcase—case number without page number
left([case no],12)

dd. pcode—physician code used for quality assurance reporting statistics
filelookup([physican.physician],[physican.pcode],[physician1])

ee. pcode2—physician code used for quality assurance reporting statistics
filelookup([physican.physician],[physican.pcode],[physician2])

ff. o—type of attending physician—surgery, obgyn, endoscopy, etc.
filelookup([physican.physician],[physican.o],[physician1])

gg. ln—determines if a lymph clearing case or not
select([gross]! "clearing","ln") else "nl"

hh. lnp—Lymph node clearing page required or not
select([ln] ! "ln","Lymph Node Clearing Page Required") else "No LN Page Required"

ii. dc—Case submitted for decalcification or not
select([gross] ! "submitted for decal","dc") else "nd"

jj. dcp—Decal page required or not
select([dc] ! "dc","Decal Page Required") else "No Decal Page Required"

kk. sn—Sentinel lymph node case or not
select([specimen1] ! "senti","sn")([specimen2] ! "senti","sn")([specimen3] ! "senti","sn")([specimen4] ! "senti","sn")([specimen5] ! "senti","sn")([specimen6] ! "senti","sn") else "ns"

ll. snp—Sentinel lymph node page required or not
select([sn]="sn","Sentinel Lymph Node Page Required") else "No Sentinel Page Required"

mm.—md—Pathologist's initials
select ([pathologist]="M. Rundell,","M R") ([pathologist]= "E. Yang,","E Y") ([pathologist]="J. Smith,","J S") ([pathologist]="L. Jones,","L J") else blank nn. clinact—Notifies physician of possible difference between pathology exam and clinical impression.

if ([prematch]="03" or [prematch]="04" or [prematch]= "05" or [prematch]="08") then "* Note: Path Dx may not coincide with clinical impression, clinical correlation is suggested." else blank oo. specact—Submitted tissue not sufficient for diagnosis.
if ([sc]="04" or [sc]="05" or [sc]="07") then "* Note: No specific pathologic diagnosis can be made. Additional tissue is required if clinically indicated." else if [sc]="09" then "* Note: Tissue adequate but no specific pathologic diagnosis can be made." else if [sc]="02" then "* Note: This specimen was improperly fixed when received." else blank pp. hcase no—Case number if special stains requested.
select([hr]="y",[prntcase]) else null qq. hreq date—Date of special stain request
select([hr]="y",today) else blank rr. htime—Time of special stain request
select([hr]="y",time) else blank ss. rholdreq—Reason case is being held
if [hr]="y" then [rhold] else null Lookup Fields have field values based on values retrieved from other fields in linked files. Instantaneous data search of hundreds to hundreds of thousands of records in related files is possible. The search can be manual, by typing the closest character match and selecting the desired record, or automatic, based on an identical match of field values in the related files and the desired information being inserted in the appropriate field without any operator action. The results from manual lookups can be overwritten, whereas the results for automatic lookups can be changed only if the lookup is a default equation or suggested valued and not a calculated field.

aa. sdl—Lookup field based on specimens in standardized case file for examining pathologist. The lookup id consisting of the physician's initials and case id is returned. Case id is utilized as a link for auto lookup of other identical fields from the standardized pathologist file into the current case. The lookup values are suggested values for their respective fields and can be overwritten by examining pathologist as necessary.

Lookup fields linked to sdl value are as follows: gross (summary of physical and microscopic pathologist exam); diagnosis (pathologist's case findings); tissue cd1; slide code; aslide; prematch; sc; cs; cty; cytomtch; t1-t5 (tissue codes representing areas of tissue sample for case); d01-d05 (disease codes corresponding to tissue samples); tumor code; tnm (tumor node metastasis indicating that size and nature of lymph node tumor); qacomment (pathologist quality assurance comments on case, if any); sec; frozen; afxmatch; mam; premam; ms; mammat; and mamact (action to take if difference above exists).

bb. t1-t5—Lookup for master tissue area file by name. A two-digit code representing the area is returned.

cc. d01-d05—Lookup for master disease file by name. A five-digit code representing the disease type is returned.

dd. abname1-5—Lookup for historical archive file by patient name. The case number of any previous exam is returned.

ee. physician—Lookup for master physician file. The attending physician name is returned.

ff. physician2—Lookup for master physician file. The attending physician name is returned.

gg. ss1-12—Lookup for master stain type file. The desired stain code is returned.

exam); afd (suggested pathologist's action for delays greater than 20 minutes); fmm (degree of difference in diagnosis from frozen specimen and final diagnosis); pathologist; sec; page (indication of last page of exam containing quality assurance statistics); tumor code (standardized code for tumor if any); tnm (tumor node metastasis); clinact (suggested notification to examining physician of possible difference with clinical impression printed on daily reports); and specact (indication of lack of adequacy of specimen for diagnosis printed on daily reports).

The daily quality assurance reports generated are shown in the following table.

| report name | title | description |
|---|---|---|
| dtsumhi | Daily Hold Case Index | Index of daily hold reports |
| dayhold | Daily Cases on Hold | Summary of daily cases on hold |
| | | Hold Review |
| dholdcss | Daily Hold Review Action | Summary of hold cases, reason for hold and action pending, if any. |
| | | Sentinal Lymph Node Hold Cases |
| sentlnd | Daily Sentinal Lymph Node Hold Cases | Summary of sentinal lymph node cases |
| | | Breast Cases on Hold |
| erpr | Breast ER/PR Cases on Hold | Summary of Breast ER/PR Cases on Hold |
| brim | Breast Implant Case on Hold | Summary of Breast Implant Cases on Hold |
| breastn | Non Malignant Breast Cases on Hold | Summary of Non Malignant Breast Cases on Hold |
| | | Prostate Cases on Hold |
| prosn | Non Malignant Prostate Case on Hold | Summary of Non Malignant Prostate Cases on Hold |
| | | Slide Cases on Hold |
| dslidpro | Slide Review Review of Hold Cases | Summary report of cases on hold for slide deficiencies |
| | | Review of Hold Cases |
| dtholdno | Hold Cases by Pathologist | Summary case report of days hold exceeding recommended threshold |
| mdholno | Hold Cases by Pathologist w page break | Same as above with page break by pathologist |

Quality Assurance Fields are where data from the various fields are summarized in historical files for trending and statistical analysis, reporting of exam correlation results by department and case origin. Quality assurance fields include tissue cd1; slide code; aslide; prematch; mam; premam; ms; mammat; mamact (indication of cases being referred to committee if diagnosis difference between examining physician and pathologist); bmark (number of breast markers in specimen); cytomtch; acyto (suggested action depending on correlation of cytology and specimen slides); sc; outside consultant; aout (suggested pathologist's action as a result of outside consultation if used); frozen; afxmatch; frozen code (number of frozen specimens); fmin (time in minutes to finish frozen specimen exam); rfd (reason for delay >20 minutes in frozen The monthly exam file includes all data transferred from the daily exam file as cases are completed. The yearly exam file includes all data transferred from the daily exam file as cases are completed. The historical archive exam file includes all data transferred from the daily exam file as cases are completed with following exceptions: specimen information, pathologist's physical and microscopic exam findings, special stain request info and any pathologist quality assurance comments. Daily reports cover completed cases transferred on a daily basis to the monthly, yearly, and historical archive files.

The monthly quality assurance reports generated are shown in the following table.

| report name | title | description |
|---|---|---|
| qaindexs | QA S Cases | Index of Monthly QA reports |
| | | Clinical vs. Pathologic Diagnosis |
| preopcfs | Case count by dept | Number and types of differences |
| monpreos | Case review report | Pre and post op diagnosis vs. final diagnosis |
| | | Breast Case Review |
| mnmsuss | Surgery dept summary breast case count | Count by physician of breast tissue type, exam correlation, suspicion levels and tumor to biopsy relationship |
| mnmsusx | X-ray dept summary breast case count | Count by physician of breast tissue type, exam correlation, suspicion levels and tumor to biopsy relationship |
| mnmsusdx | X-ray dept summary breast case count | Count by physician of breast tissue type and suspicion levels |
| mnmsums | All dept summary breast case count | Count by physician of breast tissue type and suspicion levels |
| mams | Review Report by Dept | Summary report of all breast cases including tissue and biopsy types and exam differences, if any. |
| | | Specimen Review |
| mnspecos | Summary Specimen count by Dept | Count by dept of all cases vs. cases with deficiencies |
| specos | Specimen report by Dept | Summary case report of all case with specimen deficiencies |
| | | Tissue Review |
| tisssums | Summary count by Tissue Category | Summary count of different tissue types |
| tissrevs | Tissue Report by Type | Summary case report by tissue type if type does not match exam results |
| | | Frozen Exam Review |
| mnfxmats | Summary count by Frozen Category | Summary count by type of difference between frozen tissue and final exam |
| frozens | Frozen Case vs. Final Diagnosis | Review of cases exceeding threshold for time to complete or number of frozen sections. |
| | | Cytology Review |
| moncytos | Summary count of cytology cases | Category count by dept of comparison of cytology fluid exam vs. final diagnosis |
| cytodifs | Cytology Action Report | Summary report by case when difference exists between cytology fluids and final exam |
| | | Slide review |
| monslids | Summary count by Slide Category | Summary count of slide deficiencies |
| slids | Slide Review Report by Case | Summary case report of slides with deficiencies |
| | | Review of Hold Cases |
| monholds | Hold Case Analysis Summary | Summary count by category of number of cases exceeding days hold threshold |
| holdss | Hold Case Report | Summary case report of days hold exceeding recommended threshold |
| | | Internal Review |
| monarevs | Summary count by Review Category | Summary count of cases internally reviewed by pathologist and action taken, if any |
| arevs | Action Taken Report | Summary case report if internal pathologist review does not agree with initial pathologist exam |
| | | Outside Consultant Review |
| monouts | Summary Case count sent outside | Summary count by pathologist of cases sent for outside consultation and exam differences, if any |
| outsides | Outside Consultant Case report | Summary review of all cases sent for outside consultation |

Similar reports can be generated yearly and/or over any time frame specified. In various embodiments, the daily reports and the monthly reports may be identical in form, differing only in time frame coverage. These daily reports may allow the pathologist to take prompt remedial action as necessary in exam procedures and reporting as well as streamline the required monthly reporting process. Monthly reports may be automatically sorted and printed by the required hospital departments and outside physicians or medical groups as appropriate to allow for rapid and easy dissemination of reports.

Any cases that were designated as "standards" or templates for future exam reporting of similar cases are identified and transfer to the appropriate pathologist's and the overall standards files.

Cases having slides with problems are also identified and transferred to a histology log file for further review and examination.

Case with differences between examining physician(s) diagnosis and clinical impression are transferred to a pre-match log file for further review.

The following exemplary internal reports, in addition to the individual exam reports as previously mentioned, can be printed as an internal verification of the data in the reports and a guide to additional diagnostic or examination procedures still needed. The screen view names in the following are exemplary and illustrative only.

1. Daily list of completed cases. Screenview is "dailycasetr."
2. Daily report of cytology slides by pathologist. The number of examined slides by pathologist is easily verified to ensure daily caseloads do not exceed suggested guidelines. Screenview is "cytslide#."
3. An overview of cases with differences between examining physicians' pre and post op diagnosis and the pathologist's clinical impression. Screenview is "prematchlog."
4. An overview of cases still on hold. Screenview is "dailyholdaction."
5. An overview of all sentinal lymph node cases pending further review and status verification. Screenview is "sentlnd."
6. Report of all breast cases sent to ER/PR. Screenview is "breasterpr."
7. Report of all breast implant specimens to hold indefinitely. Screenview is "Breastim."
8. Report of all non-malignant breast cases to review. Screenview is "breastn."
9. Report of all non-malignant prostrate cases to review. Screenview is "prostraten."
10. Report of all frozen cases exceeding 20 min pathologist review threshold or more than 4 frozen specimens. Screenview is "frozl."
11. Report of all selected slides with problems. Screenview is "daily slide pro."
12. Report of all cases still on hold sorted by pathologist. Screenview is "dailyholdmd."

A report may run one page or multiple pages. The last page, whichever page that is, is designated as the page with the quality assurance indicators for the case. Quality assurance reporting includes the last page of each case transferred on a monthly basis as a separate record to the quality assurance reporting database. In some cases, there may be multiple reports. In cases with multiple reports, it is possible that one case may have multiple quality assurance reports.

Although the methods and systems of various embodiments of the present invention have been described in connection with a pathology report embodiment, other embodiments are contemplated. The methods and systems are useable by any user who completes forms and could use a "shorthand" methodology. For example, law enforcement personnel may use a handheld input device to generate traffic tickets or investigation reports. The computing engine may also run background checks on drivers' license numbers or vehicle tag numbers automatically or by command code indicators. Quality management metrics, such as time required for each investigation and the number of investigations per reporting period, among others, could be tracked automatically. Updates between and among investigators could allow for improved efficiency in reporting of investigations.

In another example, contract managers may start with a services contract template with standard language. By inputting certain values in designated spaces, the computing engine could add additional contract terms based on the entries. Quality management metrics, such as time required for each contact negotiation and the number of revisions per contract, among others, could be tracked automatically.

Software embodying the techniques described above may be stored as instructions on a computer-readable non-transitory media, including, but not limited to, all forms of optical and magnetic, including solid-state, storage elements, including removable media. The computer-readable media may be included as part of a storage subsystem of a computer, either internal or external the computer.

The foregoing disclosure and description of the invention are illustrative and explanatory thereof, but to the extent foreseeable, the scope of the invention is defined by the appended claims.

We claim:

1. A system, comprising:
a database;
a report template, comprising a plurality of fields, each corresponding to one or more locations in the database;
a computer, configured to:
receive data and one or more voice commands from a user, and
store the data and one or more voice commands in the database;
generate a report based on the report template, wherein the report comprises:
at least a subset of the data, associated with one or more fields of the plurality of fields of the report template;
values retrieved from the database in response to at least one of the one or more voice commands, associated with one or more fields of the plurality of fields of the report template; and
one or more quality management indicator fields retrieved from the database and added to the report template.

2. The system of claim 1, wherein the computer is further configured to store the data in one or more selected locations in the database in response to the one or more voice commands.

3. The system of claim 1, wherein the quality management indicator fields comprise mandatory error checking fields.

4. The system of claim 1, wherein the quality management indicator fields comprise an indicator of suitability of a pathology sample for diagnosis.

5. The system of claim 1, wherein the quality management indicator fields comprise an indicator of degree of difference between a pathology specimen and a final diagnosis.

6. The system of claim 1, wherein the quality management indicator fields comprise a comparison of a cytology slide with a tissue slide.

7. The system of claim 1, wherein the computer is further configured to send the report automatically to a predetermined recipient.

8. A method comprising:
  storing in a database notes about one or more user observations, wherein the notes comprise data and one or more voice commands on how to present the one or more observations in a report;
  arranging the notes about the one or more user observations in the report based on the one or more voice commands according to a report template;
  adding one or more quality management indicator fields to the report template, based on the report template or fields filled within the report template; and
  generating the report using the report template.

9. The method of claim 8, wherein the quality management indicator fields comprises mandatory error checking fields.

10. The method of claim 8, wherein the quality management indicator fields comprise an indicator of suitability of a pathology sample for diagnosis.

11. The method of claim 8, wherein the quality management indicator fields comprise an indicator of degree of difference between a pathology specimen and a final diagnosis.

12. The method of claim 8, wherein the quality management indicator fields comprise a comparison of a cytology slide with a tissue slide.

13. The method of claim 8, further comprising:
  retrieving one or more entries from one or more databases based on the report template or fields filled within the report template; and
  adding the one or more entries to the report.

14. The method of claim 8, further comprising:
  receiving one or more user observations for inclusion in the report.

15. The method of claim 8, further comprising:
  retrieving one or more entries from one or more databases in response to a voice command of the one or more voice commands; and
  adding the one or more entries to the report.

16. A method, comprising:
  receiving a first voice command comprising an instruction to navigate to a first data entry field of a report template;
  updating the first data entry field with data received from a voice input device;
  receiving a second voice command, the second voice command comprising a first code;
  retrieving a first entry corresponding to the first code from a second database, wherein the first entry comprises a third voice command to insert a quality management indicator field from the second database into the report template;
  executing the third voice command; and
  generating a report from the report template.

17. The method of claim 16, wherein the quality management indicator field must be filled before performing the act of generating a report from the report template.

18. The method of claim 16, wherein the quality management indicator field comprises a mandatory error-checking field.

19. The method of claim 16, further comprising:
  automatically faxing the report to a predetermined recipient.

20. The method of claim 16, further comprising:
  receiving a first identifier, identifying the report template in a template database; and
  retrieving the report template from the template database.

21. A system, comprising:
  a processor;
  a storage subsystem, coupled to the processor;
  a database, stored on the storage subsystem, comprising:
    a plurality of codes; and
    a plurality of commands, each corresponding to a code of the plurality of codes; and
  software, stored on the storage subsystem, comprising instructions that when executed by the processor cause the processor to perform actions comprising:
    receiving vocally a user-supplied code, the user-supplied code one of the plurality of codes;
    retrieving a first command of the plurality of commands corresponding to the user-supplied code; and
    executing the first command,
  wherein the first command when executed causes the processor to insert a quality management indicator field into a report template.

22. A method comprising:
  navigating direct to any of a plurality of editable data fields in a template responsive to voice commands received from a user;
  updating a data field of the plurality of editable data fields responsive to voice input data received from the user;
  storing the voice input data in a database;
  inserting quality management indicator fields into a report responsive to the voice input data; and
  faxing the report automatically to a predefined recipient.

23. The method of claim 22, further comprising:
  performing quality assurance analysis on the quality management indicator fields; and
  reporting results of the quality assurance analysis.

24. The method of claim 22, further comprising:
  inserting automatic billing codes automatically responsive to the voice input data.

25. The method of claim 22, wherein the report comprises physician diagnostic reporting.

26. A method of reporting on a pathology sample received from a physician, comprising:
  retrieving a template from a database of templates, responsive to a first voice command received from a pathologist, the template defining a plurality of fields;
  navigating direct to a first field of the plurality of fields responsive to a second voice command received from the pathologist;
  retrieving a first data from a first database, the first data corresponding to an observation associated with the pathology sample;
  entering the first data into the first field;
  updating a second field of the plurality of fields with quality management indicator data calculated automatically from data contained in one or more of the plurality of fields;
  generating a pathology report from the template;
  sending the report automatically to the physician; and
  updating one or more historical databases with data contained in one or more of the plurality of fields.

27. The method of claim 26, further comprising:
  generating an historical quality management report corresponding to the physician from the one or more historical databases automatically on a periodic basis.

28. The method of claim 26, further comprising:
  generating an historical quality management report corresponding to the pathologist from the one or more historical databases automatically on a periodic basis.

29. The method of claim 26, further comprising:
  receiving a second data from the pathologist vocally; and
  updating the first field with the second data.

30. The method of claim 26, further comprising:
updating a third field of the plurality of fields with quality management indicator data received vocally from the pathologist.

31. A computer readable medium with instructions for a computer stored thereon wherein the instructions cause the computer to perform a method, comprising:
receiving notes about one or more observations from a voice input device, wherein the notes include data and one or more commands on how to present the one or more observations in the report;
storing the notes in a database;
extracting the one or more commands from the notes and arranging the notes about the one or more observations in the report based on the one or more commands according to a report template;
adding one or more quality management indicator fields to the report template, based on the template or fields filled within the template;
generating the report;
faxing the report automatically to a predefined one or more recipients.

* * * * *